United States Patent
Zhang et al.

(10) Patent No.: US 10,093,898 B2
(45) Date of Patent: Oct. 9, 2018

(54) PURIFICATION OF FUNCTIONAL HUMAN ASTROCYTES

(71) Applicant: The Board of Trustees of the Leland Stanford Junior University, Stanford, CA (US)

(72) Inventors: Ye Zhang, Menlo Park, CA (US); Steven Sloan, Palo Alto, CA (US); Ben A. Barres, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 21 days.

(21) Appl. No.: 15/158,404

(22) Filed: May 18, 2016

(65) Prior Publication Data

US 2016/0340648 A1    Nov. 24, 2016

Related U.S. Application Data

(60) Provisional application No. 62/163,884, filed on May 19, 2015.

(51) Int. Cl.
| | |
|---|---|
| *C12N 5/079* | (2010.01) |
| *A61K 39/395* | (2006.01) |
| *A61K 35/30* | (2015.01) |

(52) U.S. Cl.
CPC ............ *C12N 5/0622* (2013.01); *A61K 35/30* (2013.01); *A61K 39/39541* (2013.01); *C12N 2501/50* (2013.01); *C12N 2506/08* (2013.01)

(58) Field of Classification Search
CPC ...... C12N 5/0622; A61K 35/12; A61K 35/30; A61K 39/3955; A61K 39/39541; G01N 33/5058; G01N 33/56966
See application file for complete search history.

(56) References Cited

PUBLICATIONS

Foo et al. Neuron 71 (2011): 799-811.*
Chew et al., Finding degrees of separation: Experimental approaches for astroglial and oligodendroglial cell isolation and genetic targeting, J Neurosci Methods, Oct. 30, 2014 pp. 125-147, 30;236C, Elsevier, Atlanta, GA.
Van Strien et al., "Isolation of neural progenitor cells from the human adult subventricular zone based on expression of the cell surface marker CD271", Stem Cells Transl Med., Apr. 3, 2014, pp. 470-480, (4), AlphaMed Press, Durham, NC.
MacConald et al., "Enrichment of differentiated hNT neurons and subsequent analysis using flow-cytometry and xCELLigence sensing", J Neurosci Methods, Apr. 30, 2014, pp. 47-56, Elsevier, Amsterdam, Netherlands.
Wagley et al., "A monoclonal antibody against human MUDENG protein", Monoclon Antib Immunodiagn Immunother. Nov. 4, 2013, pp. 277-282, vol. 32, No. 4, Mary Ann Liebert, Inc., New Rochelle, NY.
Waller et al., "Isolation of enriched glial populations from postmortem human CNS material by immuno-laser capture microdissection", J Neurosci Methods, Apr. 18, 2012, pp. 108-113, 208(2), Elsevier, Amsterdam, Netherlands.

* cited by examiner

*Primary Examiner* — Robert C Hayes
(74) *Attorney, Agent, or Firm* — Pamela J. Sherwood; Bozicevic, Field & Francis LLP

(57) ABSTRACT

Compositions and methods are provided for the purification of astrocytes from biological samples or from in vitro cultures. An advantage of the methods of the invention is the ability to isolate astrocytes in a quiescent state, which allows analysis of the cells in a more natural state.

10 Claims, 7 Drawing Sheets
(7 of 7 Drawing Sheet(s) Filed in Color)

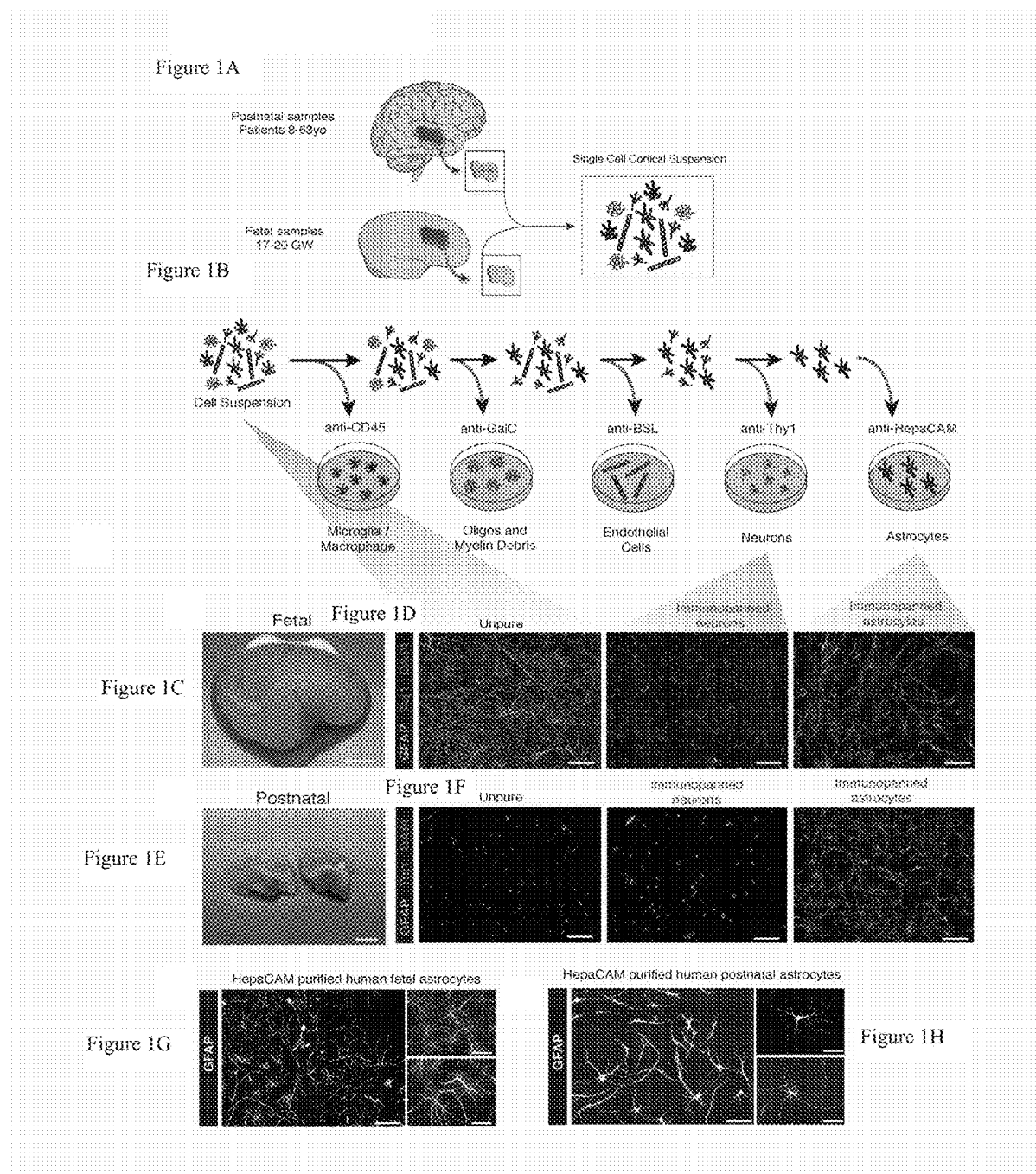

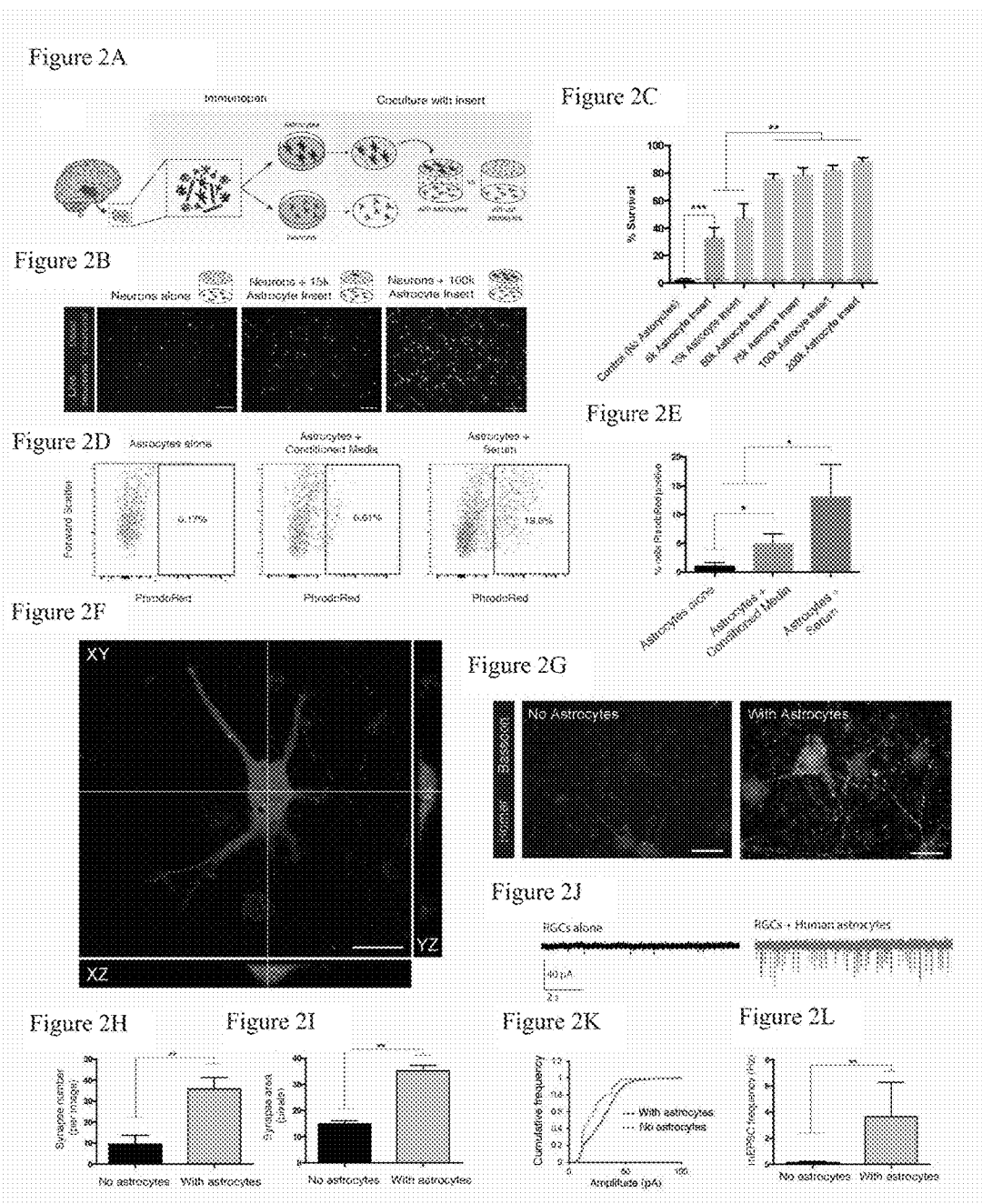

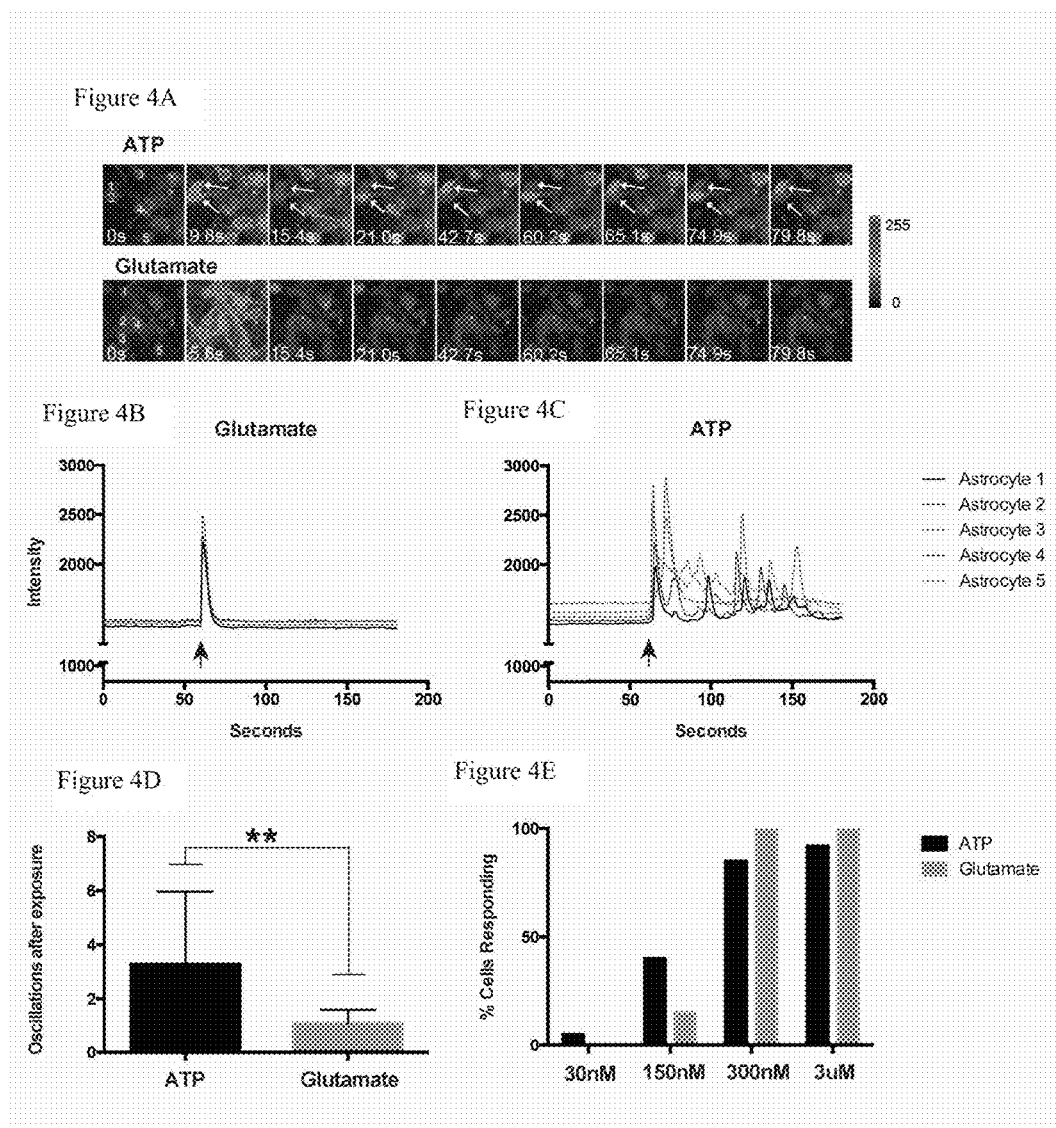

Acutely purified human astrocytes in culture

Acutely purified human astrocytes in culture + serum

PURIFICATION OF FUNCTIONAL HUMAN ASTROCYTES

FEDERALLY SPONSORED RESEARCH AND DEVELOPMENT

This invention was made with Government support under contracts MH099555 and NS081703 awarded by the National Institutes of Health. The Government has certain rights in the invention.

BACKGROUND OF THE INVENTION

Comprising about 40% of all cells in human brains astrocytes have long been classified as mere passive support cells. Recent work, however, has demonstrated that astrocytes play many active roles and are critical for the development and function of the central nervous system (CNS). For example, purified neurons in culture are incapable of forming synapses; instead, synaptogenesis proceeds only in the presence of astrocytes or astrocyte-secreted proteins. Astrocytes are not only important for the formation of synapses, but are also essential for the phagocytic elimination of synapses and the refinement of developing neural circuits. Since synapse formation and elimination are key cellular processes occurring during learning and memory, astrocytes are postulated to be an indispensable component in CNS plasticity. Additionally, astrocytes are required for neurotransmitter recycling, extracellular potassium homeostasis, regulation of blood flow, and providing energy substrates for neurons. Considering their central role in CNS physiology, it is not surprising that astrocyte dysfunction has been demonstrated or implicated in nearly all neurological disorders. But the extent of our understanding of astrocyte physiology in health and disease is almost entirely restricted to observations in rodent models. How primary human and murine astrocytes compare at molecular and functional levels remains largely unknown.

Observational studies from sectioned postmortem human tissues have revealed that human astrocytes are much larger and more complex than their rodent counterparts. Additionally, functional studies in organotypic cultures have revealed that calcium transients propagate faster in human astrocytes than in rodent astrocytes. More recently, transplantation of human glial progenitors into mouse brains have been shown to improve learning and memory in the chimeric mice. These observations raise questions about how rodent astrocyte physiology and function might extend to humans, and whether human astrocytes have distinct properties that make them better suited for contributing to the unique intelligence of humans. The roles astrocytes play in neurological disorders and development of effective therapeutic approaches to help human patients suffering from neurological disorders may depend on the ability to isolate functional human astrocytes.

A major hurdle in addressing these issues is the lack of a method to acutely purify human astrocytes and culture them in chemically defined conditions. Current purification methods for human astrocytes are based on a protocol developed by McCarthy and de Vellis over 30 years ago, which requires culturing dissociated nervous tissue in serum for days. Exposure to serum is sufficient to kill the majority of cells, except for a small population of astrocyte progenitor-like cells that survive and proliferate to eventually populate the culture. In vivo, however, quiescent astrocytes do not contact serum except upon injury and blood-brain-barrier break down, and in vitro exposure to serum has been shown to induce irreversible reactive changes in astrocytes. Moreover, since serum-selection methods require a group of proliferating astrocyte progenitors, these protocols do not work efficiently to purify mature astrocytes from adult human brains. Because of these limitations, the transcriptome profile of mature resting human astrocytes is unknown.

Deriving astrocytes from induced pluripotent stem cells or iPSCs is an attractive alternative for obtaining patient-derived astrocytes. There are a variety of protocols for differentiating iPSCs into astrocytes. However, without a transcriptome dataset of acutely purified primary human astrocytes, it is unclear whether iPSC-derived astrocytes closely resemble astrocytes in vivo and it is impossible to determine which differentiation protocol produces the best model for human astrocytes. Since iPSC-derived astrocytes are generated in weeks or months and human development happens over years, iPSC-derived astrocytes are a better model for fetal astrocytes than adult astrocytes. Therefore, there are additional challenges in modeling adult-onset neurological disorders, for example Alzheimer's disease, with iPSC-derived astrocytes.

To better understand the function and gene expression profiles of human astrocytes, and to provide a source of human astrocytes for therapeutic and research purposes, a method to acutely purify astrocytes from fetal and postnatal human brains and to culture these cells in chemically defined serum-free conditions is desirable.

SUMMARY OF THE INVENTION

Compositions and methods are provided for the purification of astrocytes from biological samples or from in vitro cultures. Compositions of greater than 95% viable primary astrocytes can be obtained. The cells can be used in drug screening assays, for therapeutic purposes, for in vitro cultures and co-cultures, and the like. In some embodiments the astrocytes are human astrocytes. An advantage of the methods of the invention is the ability to isolate astrocytes in a quiescent state, which allows analysis of the cells in a more natural state and also permits analysis during the process of activation. Quiescent cells can be isolated because the methods of the invention do not require expansion of cells by exposure to serum in vitro.

The methods of the invention utilize immunoselection to acutely purify astrocytes, e.g. from fetal, neonate, post-natal, adult, etc. brain tissue. Brain tissue may be, without limitation, human brain tissue, although the methods find use in isolating astrocytes from other mammals such as rats, mice, etc. Positive immunoselection utilizes a reagent that selectively binds to HepaCam on the cells surface. Negative immunoselection is optionally performed to deplete cells of lineages other than astrocytes, e.g. to deplete myeloid cells; oligodendrocytes and oligodendrocyte precursor cells; neurons; endothelial cells; etc. In some embodiments, negative immunoselection is performed with reagents selective for one or more of CD45; GalC, O4, Thy1 and *Banderiaea simplicifolia* lectin 1 (BSL-1). In some embodiments two, three, four, five or more negative immunoselection reagents are used, e.g. in a cocktail or in separate negative selections. Preferred selection procedures are other than flow cytometry, e.g. immunopanning, magnetic bead selection, etc.

In some embodiments, the astrocytes are derived from tissue samples, e.g. brain tissue from one or more of cerebral cortex; cerebellum; hippocampus; striatus; etc., for example a biopsy specimen, etc., where the donor may be fetal, neonate, post-natal, adult, etc. In some such embodiments, the tissue is dissociated with high concentrations of papain, e.g. at least about 1 U/ml, at least about 5 U/ml, at least about 10 U/ml, or more. The tissue may be dissociated in papain for extended periods of time, e.g. at least about 30 minutes, at least about 45 minutes, at least about 60 minutes, or longer.

A feature of the invention is the ability to generate purified and physiologically relevant astrocytes from patient samples, allowing disease-relevant generation and screening of the cells for therapeutic drugs and treatment regimens.

In some embodiments of the invention, populations of purified astrocytes, e.g. human cells, including without limitation disease-relevant astrocytes, where the cells are obtained from patient samples or are differentiated from induced human pluripotent stem cells (hiPSCs).

These and other objects, advantages, and features of the invention will become apparent to those persons skilled in the art upon reading the details of the subject methods and compositions as more fully described below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1H. Acute purification of fetal and postnatal human astrocytes. FIG. 1A. We obtained postnatal (8 to 63 years old) patient temporal lobe cortex tissue and fetal (17-20 gestational week) brain tissue and dissociate them into single cell suspensions. FIG. 1B. Schematics of immunopanning purification of cell types from human brain samples. FIG. 1C and FIG. 1E. Fetal and postnatal brain tissue. Scale bars: 5 mm. FIG. 1D and FIG. 1F. Unpurified brain cells (left), Thy1-purified neurons (middle), and HepaCAM-purified astrocytes (right) from fetal (FIG. 1D) and postnatal (FIG. 1F) brains stained at 7 div for neurons (TuJ1, red), astrocytes (GFAP, green), and nuclei of all cells (DAPI, blue). Scale bars: 100 μm. FIG. 1G and FIG. 1H. Cultured human fetal (FIG. 1G) and postnatal (FIG. 1H) astrocytes grown in culture for 7 days and stained with GFAP. Scale bars: 100 μm, insets 50 μm. See also Table 2.

FIG. 2A-2L. Functional characterization of human astrocytes. FIG. 2A. Schematics of co-culture experiments. Astrocytes and neurons were purified by immunopanning, grown in the same wells separated by porous inserts. FIG. 2B. Calcein stain of live neurons (green) and ethidium homodimer stain of dead neurons (red) in the presence and absence of astrocytes. Scale bars: 100 μm FIG. 2C. Quantification of survival rate. Data represent mean±SEM in all the figures unless otherwise noted. , $p<0.01$. *, $p<0.001$. FIG. 2D. Human astrocytes engulf synaptosomes in vitro. FACS plot of human astrocytes incubated without synaptosomes (Control), with synaptosomes and astrocyte conditioned medium (ACM), or with synaptosomes and 5% serum (Serum). FIG. 2E. Percentages of synaptosome-positive astrocytes. *, $p<0.05$. FIG. 2F. Confocal image of human astrocyte stained with GFAP (cyan) engulfing PhrodoRed labeled synaptosomes (magenta) Scale bar: 20 μm. FIG. 2G. Retinal gangion cells form more synapses in the presence of human astrocytes. Cyan: immunofluorescence of post-synaptic marker, Homer. Magenta: immunofluorescence of pre-synaptic marker, Bassoon. Scale bar: 10 μm. FIG. 2H. The number of synapses (Homer/Bassoon double positive puncta) in the presence and absence of human astrocytes. , $p<0.01$. FIG. 2I. The size of synapses in the presence and absence of human astrocytes. *, $p<0.001$. FIG. 2J. Representative traces of retinal ganglion cells cultured with or without human astrocytes in the presence of TTX. K. mini-excitatory postsynaptic current (mEPSC) amplitude. FIG. 2L. mEPSC frequency FIG. 3A-3E. Morphology of human astrocytes in vitro.

FIG. 4A-4E. Calcium response of human astrocytes in vitro. FIG. 4A. Representative images of calcium responses to ATP (top) and glutamate (bottom). Time is labeled in each image. Arrows point to two cells showing oscillatory response to ATP FIG. 4B, FIG. 4C. Fluorescence intensity of the cells labeled 1-5 in (FIG. 4A). FIG. 4D. Average number of calcium oscillations in human astrocytes after exposure to ATP or glutamate. FIG. 4E. Percentage of cells responding to various concentration of glutamate and ATP FIG. 5A-5F. RNA-seq transcriptome profiling of acutely purified human neurons, astrocytes, oligodendrocytes, microglia/macrophages, and endothelial cells.

FIG. 6A. The Zamanian et al. dataset was used to identify the top 30 reactive astrocyte genes upregulated following MCAO injury, LPS infection, or both. The expression of these genes was then probed in various astrocyte samples. Bar graphs represent the average expression of these reactive astrocyte genes (MCAO, LPS, or both) in acutely purified 'healthy' human astrocytes, epileptic samples, tumor core, tumor periphery regions, and human astrocytes obtained via serum selection methods (MD astrocytes, Lonza astrocytes, and Sciencell astrocytes). Expression is normalized to levels of mouse reactive astrocytes in ischemia and LPS injection conditions. FIG. 6B. Representative images of acutely purified human astrocytes grown in culture for 7 days without (left) or with (right) the addition of serum. Scale bar: 50 µm.

DETAILED DESCRIPTION OF THE INVENTION

Figures 3A, 3B, 3C, 3D, 3E:
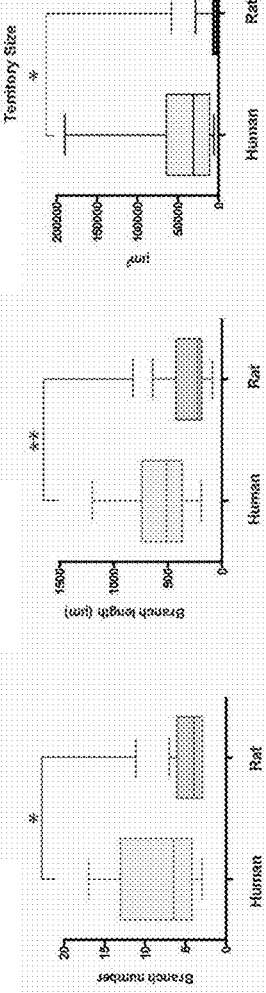
FIG. 3A. Total branch number of human and rat astrocytes grown in culture for 6 days. *$p<0.05$.
FIG. 3B. Total branch length of human and rat astrocytes grown in culture for 6 days. **$p<0.01$ FIG. 3C. Total territory size of human and rat astrocytes in culture. Territory size is defined as the 2-dimensional area that is delineated by the border of the astrocyte process (as labeled with GFAP). *$p<0.05$.
FIG. 3D, FIG. 3E. Representative human (FIG. 3D) and rat (FIG. 3E) astrocytes in serum-free media. Scale bar: 20 μm.

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "astrocytic cell," "astrocyte," etc. encompass cells of the astrocyte lineage, i.e. glial progenitor cells, astrocyte precursor cells, and mature astocytes, which for the purposes of the present invention can be isolated from native tissue, or can arise from a non-astrocytic cell by experimental manipulation. Astrocytes can be identified by markers specific for cells of the astrocyte lineage, e.g. GFAP, ALDH1L1, AQP4, EAAT1-2, etc. Markers of reactive astrocytes include S-100, VIM, LCN2, and the like. Astrocytes may have characteristics of functional astrocytes, that is, they may have the capacity of promoting synaptogenesis in primary neuronal cultures; of accumulating glycogen granules in processes; of phagocytosing synapses; and the like. A "astrocyte precursor" is defined as a cell that is capable of giving rise to progeny that include astrocytes.

Astrocytes are the most numerous and diverse neuroglial cells in the CNS. An archetypal morphological feature of astrocytes is their expression of intermediate filaments, which form the cytoskeleton. The main types of astroglial intermediate filament proteins are glial fibrillary acidic protein (GFAP) and vimentin; expression of GFAP, ALDH1L1 and/or AQP4P are commonly used as a specific marker for the identification of astrocytes.

The functions of astroglial cells are many: astrocytes create the brain environment, build up the micro-architecture of the brain parenchyma, integrate neural circuitry with local blood flow and metabolic support, maintain brain homeostasis, store and distribute energy substrates, control the development of neural cells, synaptogenesis and synaptic maintenance and provide for brain defense. As such, there is considerable interest in studying the effects of drugs and other therapeutic regimens on astrocytic cells.

In the mammalian brain the astroglial cells define the micro-architecture of the parenchyma by dividing the grey matter (through the process known as "tiling") into relatively independent structural units. The protoplasmic astrocytes occupy their own territory and create the micro-anatomical domains within the limits of their processes. Within the confines of these anatomical domains the membrane of the astrocyte covers synapses and neuronal membranes, as well as sends processes to plaster the wall of the neighboring blood vessel with their endfeet. The complex astrocyte-neurons-blood vessel is generally known as a neurovascular unit.

Astroglial cells can control extracellular homeostasis in the brain. By virtue of multiple molecular cascades, astrocytes control concentrations of ions, neurotransmitters and metabolites and regulate water movements. Glutamate is the major excitatory neurotransmitter in the brain of vertebrate, however when released in excess or for long-time, glutamate acts as a neurotoxin. Astrocytes remove the bulk of glutamate from the extracellular space by excitatory amino acid transporters (EAAT). Five types of EAATs are present in the human brain; the EAAT1 and EAAT2 are expressed almost exclusively in astrocytes, which utilize the energy saved in the form of transmembrane $Na^+$ gradient. Astroglial glutamate transport is crucial for neuronal glutamatergic transmission by operating the glutamate-glutamine shuttle. Glutamate, accumulated by astrocytes is enzymatically converted into glutamine by the astrocytic-specific glutamine synthetase. It is also of importance that astrocytes possess the enzyme pyruvate carboxylase, and thus act as a main source for de novo glutamate synthesis.

Astroglia regulate formation, maturation, maintenance, and stability of synapses, thus controlling the connectivity of neuronal circuits. Astrocytes secrete numerous factors required for synaptogenesis. Synaptic formation depends on cholesterol produced and secreted by astrocytes. Glial cells also affect synaptogenesis through signals influencing the expression of agrin and thrombin. Subsequently, astrocytes control maturation of synapses through several signaling systems, which affect the postsynaptic density, for example by controlling the density of postsynaptic receptors. Astroglia factors that affect synapse maturation include activity-dependent neurotrophic factor (ADNF). Astrocytes may also limit the number of synapses.

Astrocytes and other glial cells can release a variety of transmitters into the extracellular space, including glutamate, ATP, GABA and D-serine. Mechanisms of release may include: diffusion through high-permeability channels (e.g. volume-activated Cl-channels, unpaired connexin "hemichannels" or P2X7 pore-forming purinoceptors; through transporters, e.g. by reversal of excitatory amino acid transporters or exchange via the cystine-glutamate antiporter or organic anion transporters.

Astrocytes are involved in all types of brain pathologies from acute lesions (trauma or stroke) to chronic neurodegenerative processes (such as Alexander's disease, Alzheimer's disease, Parkinson's disease, multiple sclerosis and many others) and psychiatric diseases. Pathologically relevant neuroglial processes include various programs of activation, which are essential for limiting the areas of damage, producing neuro-immune responses and for the post-insult remodeling and recovery of neural function. Astroglial degeneration and atrophy in the early stages of various neurodegenerative disorders may be important for cognitive impairments.

In addition to various uses as in vitro cultured cells, the astrocytes may be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether the administered cells or progeny thereof are still present, and may be phenotyped for response to a treatment of interest. Suitability can also be determined in an animal model by assessing the degree of recuperation that ensues from treatment with the differentiating cells of the invention.

Brain tissue sample. The term "brain sample" as used herein, refers to a sample obtained from an individual, e.g. a human, rodent, etc. The brain sample can be obtained from the individual by routine measures known to the person skilled in the art, i.e., biopsy (taken by aspiration or punctuation, excision or by any other surgical method leading to biopsy or resected cellular material). For those areas not easily reached via an open biopsy, a surgeon can, through a small hole made in the skull, use stereotaxic instrumentation to obtain a "closed" biopsy. Stereotaxic instrumentation allows the surgeon to precisely position a biopsy probe in three-dimensional space to allow access almost anywhere in the brain. Therefore, it is possible to obtain tissue for the methods of the present invention.

Astrocytes are present in different regions of the brain, and may have varying functionality depending on the region. Samples of interest may be obtained, for example, from cerebral cortex, cerebellum, hippocampus, mesencephalon, striatum, retina, and the like. The tissue may be fetal, neonate, post-natal, juvenile, adult, etc. The tissue may be obtained from an individual with a condition of interest, e.g. epilepsy, astrocyte-associated conditions as described here in, and the like.

Alternatively, a source of astrocytes is a complex population generated in vitro, e.g. differentiated from pluripotent cells. A source of such cells is described in co-pending patent application entitled "FUNCTIONAL ASTROCYTES AND CORTICAL NEURONS FROM INDUCED PLURIPOTENT STEM CELLS AND METHODS OF USE THEREOF", herein specifically incorporated by reference.

Disease relevance. A number of pathologies are associated with astrocyte dysfunction, including Rett syndrome, fragile X mental retardation, Alexander's disease, and others. For example, amyotrophic lateral sclerosis (ALS) and/or frontotemporal dementia have implicated astrocyte dysfunction as potential drivers of these diseases. Rett syndrome, an X-linked neurodevelopmental disorder, is caused by the loss of the transcriptional repressor methyl-CpG-binding protein 2 (MeCP2.) Clinical features of the disease include autism, respiratory abnormalities, cognitive impairment, loss and regression of early developmental milestones, and a decrease in brain weight and volume. Evidence suggests that loss of MeCP2 function in astrocytes contributes to the developmental defects in neurons.

Fragile X syndrome, the most common cause of inherited intellectual disability, is caused by mutation of FMR1. Patients show cognitive impairment, autistic features, attention deficits, increased rates of epilepsy, and motor abnormalities. In humans, polyglutamine repeats in the FMR1 gene lead to loss of FMRP protein expression. Recent immunohistochemical studies demonstrate FMRP expression in developing astrocytes in vitro and possibly in vivo as well. Hippocampal neurons grown on FMR1-deficient astrocytes show abnormal dendritic morphology relative to those grown on wild-type astrocytes, and the intrinsic dendritic defects of FMR1-deficient neurons are significantly rescued when these cells are grown on a monolayer of wild type rather than FMR1-deficient astrocytes. The in vivo defects in dendritic spine development may be related to neuron-glia interactions during development.

Alexander's disease is due to a mutation in the astrocyte-specific protein GFAP. Clinically, it is characterized by macrocephaly, abnormal white matter, and developmental delay and is most commonly diagnosed in its infantile form, with onset before 2 years of age. The cardinal pathologic finding is cytoplasmic GFAP aggregates in astrocytes. Some individuals with GFAP point mutations have later onset or less severe symptoms than others.

The lysosomal storage disorder Niemann-Pick type C disease is caused by mutations in NPC1, which is localized primarily in astrocytic processes, and NP-C-deficient astrocytes showed some defects in cholesterol metabolism in culture.

Another broad category of neurological disorders that may involve astrocytes are the "RASopathies." These affect components of the Ras/MapK signaling pathway and include neurofibromatosis type-1 and Noonan, Leopard, CFC, and Costello syndromes. Clinical features across these disorders are variable, but frequently include varying degrees of neurocognitive delay. Studies in animal models suggest that signal dysregulation in these genetic diseases alters the timing of astrogliogenesis.

A neurocognitive disorder that may also involve timing of astrocyte development is Down syndrome (Trisomy 21). Recent work has shown that human neural progenitors from Down syndrome patients show a gliogenic shift and corresponding decrease in neurogenesis.

Mature and reactive astrocytes are involved in epileptogenesis via their effects on glutamate transport and release and their roles in buffering potassium and interstitial volume control. Astrocyte dysfunction in adult model systems can be involved in abnormal neuronal excitability, and inducing reactive astrocytosis can lead to the formation of epileptic foci in the hippocampus.

Autism spectrum disorders (ASDs) are neurodevelopmental disorders characterized by varying degrees of impaired social interaction and communication. Models of ASD emphasize the idea that abnormal synapse development underlies many features of the disease and postulate abnormalities in excitatory-inhibitory balance. A better understanding of astrocyte function or dysfunction in ASDs will shed light on pathogenesis and the development of new treatment strategies.

Changes in glial cell number or characteristics in the adult brains of patients with psychiatric disorders or in mouse models, including reductions in GFAP levels in prefrontal cortical and cortico-limbic areas in a rat model of depression and decreases in glial density in the amygdala in post-mortem samples of patients with depression. Recent evidence favors a developmental model of these diseases, particularly schizophrenia. Schizophrenia is defined by the presence of psychosis among other symptoms, and multiple lines of evidence support the idea that cortical "dysconnectivity," as a result of aberrant pre- or post-natal development, may be responsible for psychotic symptoms. Further attention to the roles of astrocytes is warranted, given their roles in postnatal synaptogenesis and myelination.

A recurrent theme in psychiatric diseases is the preferential dysfunction in specific brain regions, such as the prefrontal cortex, limbic system, and hippocampus. Many imaging studies have demonstrated volumetric changes in specific brain regions that could be related to glial cell loss or hypertrophy. Even more notable, noninvasive functional brain imaging techniques such as fMRI rely on measurements of neurovascular coupling (changes in blood flow to neurons), which occurs through astrocyte intermediates. Understanding the molecular and developmental basis for astrocyte regional heterogeneity may elucidate why and how specific brain regions or circuits are affected in different psychiatric diseases.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

Specific Binding Member.

The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. Such specific binding members are useful in positive and negative selection methods. Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; etc. The specific binding pairs may include analogs, derivatives and fragments of the original specific binding member. For example, a receptor and ligand pair may include peptide fragments, chemically synthesized peptidomimetics, labeled protein, derivatized protein, etc.

Especially useful reagents are antibodies specific for markers present on the desired cells (for positive selection) and undesired cells (for negative selection). Alternatively lectins can be used for selection. Whole antibodies may be used, or fragments, e.g. Fab, F(ab)$_2$, light or heavy chain fragments, etc. Such selection antibodies may be polyclonal or monoclonal and are generally commercially available or alternatively, readily produced by techniques known to those skilled in the art. Antibodies selected for use will have a low level of non-specific staining and will usually have an affinity of at least about 100 µM for the antigen.

In one embodiment of the invention, antibodies for selection are coupled to a plate, bead, magnetic reagent, and the like. The exact method for coupling is not critical to the practice of the invention, and a number of alternatives are known in the art. Direct coupling attaches the antibodies to the plate, particles, magnetic reagent, etc. Indirect coupling can be accomplished by several methods. The antibodies may be coupled to one member of a high affinity binding system, e.g. biotin, and the particles attached to the other member, e.g. avidin. One may also use second stage antibodies that recognize species-specific epitopes of the antibodies, e.g. anti-mouse Ig, anti-rat Ig, etc. Indirect coupling methods allow the use of a single magnetically coupled entity, e.g. antibody, avidin, etc., with a variety of separation antibodies.

Markers of interest for selection of astrocytes include positive selection markers that selectively bind to molecules present on the surface of astrocytes, and negative selection markers that selectively bind to molecules present on cells in, for example, brain tissue, where such cells include without limitation myeloid cells such as microglia and macrophages; oligodendrocytes and oligodendrocyte precursors; neurons; endothelial cells, and the like.

A positive selection marker for astrocytes is hepatocyte and glial cell adhesion molecule, HepaCAM, which corresponds to the human protein refseq NP_689935. The HepasCAM protein, also referred to as GlialCAM, is a single-pass type I membrane protein that localizes to the cytoplasmic side of the cell membrane. The encoded protein acts as a homodimer and is involved in cell motility and cell-matrix interactions.

A negative selection marker useful for depleting leukocytes, including macrophages and microglia, is CD45 (common leukocyte antigen). CD45 is a receptor-linked protein tyrosine phosphatase that is expressed on all leucocytes The CD45 family consists of multiple members that are all products of a single complex gene containing 34 exons alternatively spliced to generate up to eight different protein products. A pan-CD45 reagent may be used, or a reagent selective for, for example, CD45RB, which is highly expressed in microglia; and/or CD45RO which is expressed in activated microglia and macrophages.

For depletion of neurons, Thy1 (CD90) can be used as a negative selection marker. CD90 is a 25-37 kDa heavily N-glycosylated, glycophosphatidylinositol (GPI) anchored conserved cell surface protein with a single V-like immunoglobulin domain. It is a marker for a variety of stem cells and for the axonal processes of mature neurons.

For depletion of oligodendrocytes, Galactosylceramidase (GalC) is a useful marker. It is a lysosomal enzyme involved in the catabolism of galactosylceramide, a major lipid in myelin, kidney, and epithelial cells of the small intestine and colon. The anti-oligodendrocyte marker 4 (O4), (for example available as clone 81, Stem Cell Technologies) is useful in the negative selection of oligodendrocyte precursor cells.

Griffonia (Bandeiraea) *Simplicifolia* Lectin (BSL1) has affinity for α-d-galactosyl andN-acetyl galactosaminyl residues, and in the brain shows prominent binding to blood vessel endothelia.

Methods of the Invention

Functionally relevant astrocytes are purified from tissue samples or from cultures. The purified cell populations are useful in analysis of gene expression, drug screening assays, for therapeutic purposes, for in vitro cultures and co-cultures, and the like. A benefit of the methods of the invention is that the astrocytes can be purified in the absence of expansion ex vivo in the presence of serum. Such in vitro expansion has been shown to activate astrocytes. The the ability to isolate astrocytes in a quiescent state allows analysis of the cells in a more natural state and also permits analysis during the process of activation. Optionally the astrocyte population thus obtained can be activated by exposure to an effective dose of a suitable agent, including, for example, serum; and other growth factors, e.g. TNFα, CNTF, FGF1, interferons, and the like.

The cell compositions thus obtained are highly purified, where the desired cells, e.g. astrocytes, quiescent astrocytes, etc. The cell population may be at least about 50% of the desired cell type, at least about, at least about 75%, at least about 80%, at least about 90%, at least about 95%, or more. Transcriptional profiling has demonstrated that quiescent astrocytes can be obtained with these methods, and that the human cells have a transcriptional profile distinct from that of rodent cells.

The methods of the invention utilize immunoselection to acutely purify astrocytes, e.g. from fetal, neonate, post-natal, adult, etc. brain tissue. Brain tissue may be, without limitation, human brain tissue, although the methods find use in isolating astrocytes from other mammals such as rats, mice, etc.

In some embodiments, the astrocytes are derived from tissue samples, e.g. brain tissue from one or more of cerebral cortex, cerebellum, hippocampus, mesencephalon, striatum, retina; etc., for example a biopsy specimen, etc., where the donor may be fetal, neonate, post-natal, adult, etc. In some such embodiments, the tissue is dissociated with high concentrations of papain, e.g. at least about 1 U/ml, at least about 5 U/ml, at least about 10 U/ml, or more. The tissue may be dissociated in papain for extended periods of time, e.g. at least about 30 minutes, at least about 45 minutes, at least about 60 minutes, or longer. In other embodiments a complex cell population comprising astrocytes is generated by in vitro differentiation.

For positive or negative selection, separation of the subject cell population utilizes affinity separation to provide a substantially pure population. Techniques for affinity separation may include magnetic separation using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Any technique may be employed which is not unduly detrimental to the viability of the cells.

Positive immunoselection utilizes a reagent that selectively binds to HepaCam on the cells surface. Negative immunoselection is optionally performed to deplete cells of lineages other than astrocytes, e.g. to deplete myeloid cells; oligodendrocytes and oligodendrocyte precursor cells; neurons; endothelial cells; etc. In some embodiments, negative immunoselection is performed with reagents selective for one or more of CD45; GalC, O4, Thy1 and *Banderiaea simplicifolia* lectin 1 (BSL-1). In some embodiments two, three, four, five or more negative immunoselection reagents are used, e.g. in a cocktail or in separate negative selections. In some embodiments, a lineage cocktail comprising reagents for negative selection of each of myeloid cells; oligodendrocytes and oligodendrocyte precursor cells; neurons; endothelial cells. Where negative separation is used, it is usually performed prior to the positive selection, in order to deplete the cell population of undesirable cells. A positive selection is then performed.

Specific binding members, usually antibodies or lectins, are added to the suspension of cells, and incubated for a period of time sufficient to bind the available antigens. The incubation will usually be at least about 2 minutes and can be less than about 30 minutes. It is desirable to have a sufficient concentration of antibodies or lectins in the reaction mixture so that the efficiency of the separation is not limited by lack of reagent. The appropriate concentration is determined by titration.

In some embodiments the selection reagents are bound to a plate or other planar surface, in which case a cell suspension is added to the surface. In other embodiments the selection reagent is bound to a particle, e.g. bead, magnetic particle, etc., and which case the suspension of cells can be admixed with the selection reagent.

In a negative selection, the unbound cells are collected; in a positive selection, the bound cells are collected. The unbound cells contained in the eluate may be collected as the eluate passes through a separation device, or released from a plate or other planar surface. Bound cells can be released by gentle protease digestion, EDTA, and the like. The medium in which the cells are separated will be any medium which maintains the viability of the cells. A preferred medium is serum-free, for example Neurobasal DMEM serum-free medium; phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., preferably in the absence of serum.

The compositions thus obtained have a variety of uses in clinical therapy, research, development, and commercial purposes. For therapeutic purposes, for example, astrocytes may be administered to enhance tissue maintenance or repair for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and maintain their phenotype in vivo.

Cell compositions are administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or β-galactosidase); that have been prelabeled (for example, with BrdU or [$^3$H] thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

The astrocytes may be used for tissue reconstitution or regeneration in a human patient or other subject in need of such treatment. The cells are administered in a manner that permits them to graft or migrate to the intended tissue site and reconstitute or regenerate the functionally deficient area. The cells may be administered in any physiologically acceptable excipient. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or feeder cells associated with progenitor cell proliferation and differentiation.

The cells of this invention can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

Cells may be genetically altered in order to introduce genes useful in the differentiated cell, e.g. repair of a genetic defect in an individual, selectable marker, etc., or genes useful in selection against undifferentiated ES cells. Cells may also be genetically modified to enhance survival, control proliferation, and the like. Cells may be genetically altering by transfection or transduction with a suitable vector, homologous recombination, or other appropriate technique, so that they express a gene of interest. In some embodiments, a selectable marker is introduced, to provide for greater purity of the desired cell. Cells may be genetically altered using vector containing supernatants over a 8-16 h period, and then exchanged into growth medium for 1-2 days. Genetically altered cells are selected using a drug selection agent such as puromycin, G418, or blasticidin, and then recultured.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells (see Uchida et al. (1998) *P.N.A.S.* 95(20): 11939-44).

Screening Assays

Methods are also provided for determining the activity of a candidate agent on astrocytes, e.g. to determine toxicity, to determine the effect on a disease-relevant cell, etc. the method comprising contacting the candidate agent with one or a panel of purified astrocytes; and determining the effect of the agent on morphologic, genetic or functional parameters, including without limitation gene expression profiling.

In screening assays for the small molecules, the effect of adding a candidate agent to cells in culture is tested with a panel of cells and cellular environments, where the cellular environment includes one or more of: electrical stimulation including alterations in ionicity, stimulation with a candidate agent of interest, contact with other cells including without limitation neurons and neural progenitors, and the like, and where panels of astrocytes may vary in genotype, in prior exposure to an environment of interest, in the dose of agent that is provided, etc. Usually at least one control is included, for example a negative control and a positive control. Culture of cells is typically performed in a sterile environment, for example, at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free. The effect of the altering of the environment is assessed by monitoring multiple output parameters, including morphogical, functional and genetic changes.

In the screening assays for genetic agents, polynucleotides can be added to one or more of the cells in a panel in order to alter the genetic composition of the cell. The output parameters are monitored to determine whether there is a change in phenotype. In this way, genetic sequences are identified that encode or affect expression of proteins in pathways of interest. The results can be entered into a data processor to provide a screening results dataset. Algorithms are used for the comparison and analysis of screening results obtained under different conditions.

Methods of analysis at the single cell level are of particular interest, e.g. as described above: atomic force microscopy, single cell gene expression, single cell RNA sequencing, calcium imaging, flow cytometry and the like. Various parameters can be measured to determine the effect of a drug or treatment on the astrocytes.

Parameters are quantifiable components of cells, particularly components that can be accurately measured, desirably in a high throughput system. A parameter can also be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Cardiovascular Drugs; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; RNAi, encode a dominant negative mutation, or dominant or constitutively active mutations of native sequences; altered regulatory sequences, etc.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Agents are screened for biological activity by adding the agent to at least one and usually a plurality of cells, in one or in a plurality of environmental conditions, e.g. following stimulation with a β-adrenergic agonist, following electric or mechanical stimulation, etc. The change in parameter readout in response to the agent is measured, desirably normalized, and the resulting screening results may then be evaluated by comparison to reference screening results, e.g. with cells having other mutations of interest, normal astrocytes, astrocytes derived from other family members, and the like. The reference screening results may include readouts in the presence and absence of different environmental changes, screening results obtained with other agents, which may or may not include known drugs, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure.

Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The comparison of screening results obtained from a test compound, and a reference screening results(s) is accomplished by the use of suitable deduction protocols, AI systems, statistical comparisons, etc. Preferably, the screening results is compared with a database of reference screening results. A database of reference screening results can be compiled. These databases may include reference results from panels that include known agents or combinations of agents, as well as references from the analysis of cells treated under environmental conditions in which single or multiple environmental conditions or parameters are removed or specifically altered. Reference results may also be generated from panels containing cells with genetic constructs that selectively target or modulate specific cellular pathways.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

For convenience, the systems of the subject invention may be provided in kits. The kits could include the cells to be used, which may be frozen, refrigerated or treated in some other manner to maintain viability, reagents for measuring the parameters, and software for preparing the screening results. The software will receive the results and perform analysis and can include reference data. The software can also normalize the results with the results from a control culture. The composition may optionally be packaged in a suitable container with written instructions for a desired purpose, such as screening methods, and the like.

Of particular interest is the examination of gene expression in the astrocyte populations of the invention. The expressed set of genes may be compared against other subsets of cells, for example activated astrocytes, rodent astrocytes, against ES cells, against developing brain tissues, and the like, as known in the art. Any suitable qualitative or quantitative methods known in the art for detecting specific mRNAs can be used. These can be measured by sequencing, PCR amplification, hybridization techniques, and the like as known in the art. One of skill in the art can readily use these methods to determine differences in the identity, size or amount of mRNA transcripts between two samples. Any suitable method for detecting and comparing mRNA sequences and expression levels in a sample can be used in connection with the methods of the invention.

The astrocytes of this invention can also be used to prepare antibodies that are specific for markers of astrocytes and their precursors. Polyclonal antibodies can be prepared by injecting a vertebrate animal with cells of this invention in an immunogenic form. Production of monoclonal antibodies is described in such standard references as U.S. Pat. Nos. 4,491,632, 4,472,500 and 4,444,887, and Methods in Enzymology 73B:3 (1981). Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

The antibodies in turn can be used to identify or rescue cells of a desired phenotype from a mixed cell population, for purposes such as costaining during immunodiagnosis using tissue samples, and isolating precursor cells from terminally differentiated astrocytes and cells of other lineages.

For further elaboration of general techniques useful in the practice of this invention, the practitioner can refer to standard textbooks and reviews in cell biology, tissue culture, embryology, and neurobiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Example 1

Acute Purification and Transcriptome Profiling of Human Astrocytes

Astrocytes play critical roles in the development and function of the central nervous system. However, our understanding of astrocyte physiology is largely predicated on research in rodent models. Surprisingly, the degree to which rodent and human astrocytes are comparable remains relatively unknown. We developed an immunopanning-based method to acutely purify astrocytes from fetal and postnatal human brains without the need to expand these cells in vitro via exposure to serum. Functionally, we found that similar to rodent astrocytes, human astrocytes are capable of promoting neuronal survival, inducing synapse formation, and engulfing synaptosomes. Furthermore, human astrocytes exhibit distinct calcium responses to ATP and glutamate. To uncover the human astrocyte transcriptome, we performed RNA-sequencing of acutely purified astrocytes and compared these data to purified human neurons, oligodendrocytes, microglia and endothelial cells. Our purification method and transcriptome dataset provide new resources for investigating the function of human astrocytes in healthy and diseased brains.

The method we present here is an immunopanning-based technique that utilizes an antibody targeted against HepaCAM (or GlialCAM), a surface protein expressed on human astrocytes, to generate purified (>95%) cultures of primary human astrocytes. Using this protocol, we acutely purified astrocytes from over a dozen fetal and postnatal human subjects and found that human astrocytes maintain extensive process-bearing morphologies in vitro and have gene expression profiles of resting astrocytes, in contrast to the reactive signatures of astrocytes obtained with serum-based enrichment methods. To understand the function of human astrocytes, we performed co-culture experiments with neurons and found that human astrocytes promote neuronal survival, induce synapse formation, and engulf synaptosomes in vitro. Furthermore, calcium imaging of acutely purified human astrocytes revealed that these cells respond to both ATP and glutamate, though with differing dynamics. We obtained gene expression profiles of human astrocytes by performed RNA-sequencing (RNA-seq) of acutely purified human astrocytes, as well as human neurons, oligodendrocytes, microglia, and endothelial cells. Although many human astrocyte-specific genes are shared with rodent astrocytes, we also discovered distinct gene expression signatures that may shed new light on the evolution of brain functions and facilitate translational research of human neurological disorders. Finally, we generated a user-friendly searchable online database of the gene expression profiles of acutely purified human astrocytes, neurons, oligodendrocytes, myeloid cells, and endothelia to enable dissemination of human cell type specific gene expression data.

Results

Acute purification of fetal and postnatal human astrocytes. We obtained postnatal human brain tissue samples from patients undergoing neurological surgeries with informed consent under a Stanford University Institutional Review Board approved protocol. The samples used in this study (except for FIG. 6 epilepsy, tumor, and tumor peripheral data) were small pieces of healthy temporal lobe cortices that were resected to access deeper epileptic hippocampi (FIG. 1E). In all of these cases, the temporal lobe cortices that were removed were considered normal based upon MRI imaging, EEG studies, and pathological examination. We also obtained gestational week 17-20 fetal brain tissue samples from elective pregnancy terminations (FIG. 1C). We first sought to identify an astrocyte specific antibody that we could use to immunopan human cortical tissue. We mined our existing rodent astrocyte RNAseq datasets for potential surface markers that were enriched in astrocytes and conserved to human. After screening numerous candidates, we settled on HepaCAM, a cell adhesion glycoprotein expressed specifically in astrocytes. The immunopanning protocol involves passing a single cell suspension of dissociated tissue over a series of petri dishes coated with antibodies directed against cell type specific antigens (FIGS. 1 A and B). For postnatal samples, our immunopanning protocol consisted of anti-CD45 antibodies to bind myeloid cells (microglia and macrophages), anti-GalC hybridoma to bind oligodendrocytes and myelin debris, anti-O4 hybridoma to bind oligodendrocytes and oligodendrocyte precursor cells (OPCs), anti-Thy1 antibody to bind neurons, anti-HepaCAM antibody to bind astrocytes, and *Banderiaea simplicifolia* lectin 1 (BSL-1) to bind endothelial cells. We used a shortened antibody binding procedure for fetal samples because oligodendrocytes and myelin are not yet generated at 17-20 gestational weeks (detailed in Experimental Procedures). After cells were bound to the antibody-coated dish, we washed away loosely bound contaminating cells and then either detached cells via trypsin digestion for culture or scraped cells directly off the dish in Qiazol reagent (Qiagen) to extract RNA for RNA-seq (within about 4 hours of tissue resection).

We routinely obtained over 95% pure postnatal human astrocytes as determined by GFAP immunofluorescence (FIG. 1F) and validated these immunohistochemical purity estimates by RNA-seq (FIG. 5 and see below). Postnatal human astrocytes exhibit process-bearing morphology (FIGS. 1D-H and FIG. 3) and remain healthy for weeks in vitro cultured in a serum-free defined media. Interestingly, while fetal human astrocytes proliferate in vitro, postnatal astrocytes obtained from 8 to 63 year old patients did not divide. This is further confirmed by the expression of two mitotic markers, TOP2A and MKI67, whose expression was exclusively limited to fetal astrocytes (TOP2A: FPKM 32.2+/−8.6 in fetal astrocytes 0.1+/−0 in adult; MKI67: FPKM 38.2+/−18.9 in fetal astrocytes, 0.1+/−0 in adult. Data represent average+/−SEM). In the mouse cerebral cortex, astrocytes stop proliferating around postnatal day 14 (P14) and remain non-proliferative throughout life except after injury. Therefore, the propensity of quiescent astrocytes to stop proliferating at early postnatal stages is conserved from mouse to humans. Due to their proliferative nature, acutely purified human fetal astrocytes can be frozen, stored, and defrosted at a later time. Frozen and defrosted fetal astrocytes remain healthy and continue to proliferate in culture. Therefore, experiments using immunopanned human fetal astrocytes are not time-locked to tissue availability.

Human astrocytes promote neuron survival. Our purification technique allowed us to investigate the functional capabilities of primary human astrocytes in vitro. We first tested whether human astrocytes could promote neuronal survival. We immunopanned human neurons and astrocytes (FIG. 1A) and grew them together in the same cell culture wells on separate layers. The inserts separating the two cell types have 1 µm diameter holes that allow secreted molecules to freely diffuse while preventing direct astrocyte to neuron contact (FIG. 2A). After 5 days of co-culture, we stained live neurons with calcein-AM and dead neurons with ethidium homodimer-1 (FIG. 2B). We found that human astrocytes strongly promoted neuron survival in a dose-dependent manner (Neuron survival: 2.2±0.9% without astrocytes. 88.5±2.4% with 200 k astrocytes. Data represent average±SEM. FIG. 2C.)

Human astrocytes promote synapse formation. To assess whether human astrocytes promote synapse formation, we co-cultured human astrocytes with rat retinal ganglion cells (RGCs) using inserts to separate the two cell types. We chose rat RGCs because our group has previously developed a culture medium that supports RGC survival without astrocytes. Since most CNS neurons cannot survive in purified cultures RGCs provide a unique opportunity to compare synapse numbers formed in the presence or absence of astrocytes. After co-culturing astrocytes with RGCs for 14 days, we performed immunostaining against the presynaptic marker, Bassoon and postsynaptic marker, Homer to quantify colocalized synaptic puncta. At the immunohistological level, we found that human astrocytes increased both the number and size of synapses (FIGS. 2D,F, and G. Synapse number: 9.5±4.3 per image without astrocytes; 35.8±5.5 per image with astrocytes. Synapse size: 14.8±1.3 pixels without astrocytes; 35.2±2.1 pixels with astrocytes.). To examine whether the synapses induced by human astrocytes are functional and to validate the synaptogenic effect of human astrocytes, we performed patch-clamp recordings of neurons. All recordings were performed in the presence of tetrodotoxin to isolate spontaneous postsynaptic events. Consistent with our immunohistochemical observations, we found that human astrocytes robustly increased the amplitude and frequency of mini-excitatory postsynaptic currents (mEPSCs) (FIGS. 2 E, H, and I. mEPSC frequency: 0.14±0.04 Hz without astrocytes; 3.6±1.5 with astrocytes. mEPSC amplitude: 22.2±2.1 without astrocytes; 29.5±0.5 with astrocytes.).

Human astrocytes engulf synaptosomes. Recent work suggests that rodent astrocytes are involved in eliminating extra synapses and refining neural circuits. To address whether human astrocytes share similar capabilities, we performed an in vitro synaptosome engulfment assay. We purified synaptosomes and labeled them with a fluorescent dye, PhrodoRed. PhrodoRed is almost non-fluorescent at neutral pH and fluoresces brightly in acidic environments; it therefore allowed us to detect engulfed synaptosomes that have been trafficked to lysosomes with minimal background fluorescence from sticky synaptosomes attached to the astrocyte surface. We fed human astrocytes PhrodoRed labeled synaptosomes in the presence of astrocyte-conditioned medium (ACM) or serum, which contain low and high concentrations, respectively, of bridging molecules required for phagocytosis. We then performed fluorescence assisted cell sorting (FACS) to analyze the percentage of cells with PhrodoRed fluorescence. We found that human astrocytes efficiently engulf synaptosomes in vitro in a bridging molecule dependent manner (FIGS. 2 J and K, percentage of PhrodoRed positive cells: control 1.0±0.4%; ACM 4.8±1.1%; serum 13.0±3.3%.).

Human astrocytes have a more complex morphology than rodent astrocytes in vitro. Previous studies found that human astrocytes are larger than rodent astrocytes in vivo. We wondered whether the size of human astrocytes is determined by intrinsic qualities of the astrocytes or via non-cell autonomous mechanisms. To distinguish between these possibilities, we purified human and rat astrocytes by immunopanning, cultured them in the same serum-free culture medium at comparable densities, and quantified the length of processes at 5-6 days in vitro (div). We found that the total arborization length of human astrocytes were significantly greater than rat astrocytes in vitro (FIG. 3. Average total human astrocyte process length: 566±56 µm. Average total rat astrocyte process length: 290±53 µm). Additionally, human astrocytes had on average almost twice the number of branches as rodent astrocytes (Human: 8.5±1.1, rodent: 4.5±0.5) indicating that intrinsic differences contribute, at least in part, to the larger size of human astrocytes compared with rodent astrocytes.

Human astrocytes exhibit distinct calcium response patterns to ATP and glutamate stimulation. Rodent astrocytes respond to sensory input via elevations of intracellular calcium concentrations. Astrocyte calcium transients have been proposed to be important for synaptic transmission, plasticity, and regulation of blood flow, although the actual consequences of astrocytic calcium transients are still debated. Purified rodent astrocytes exhibit calcium transients in response to ATP and glutamate stimulation in vitro. It is unclear, however, whether purified human astrocytes are responsive to ATP and glutamate. Therefore, we performed calcium imaging on purified human astrocytes after loading cells grown in vitro with the calcium sensitive dye Fluo-4 AM. We found that fetal human astrocytes responded to ATP but not to glutamate stimulations whereas postnatal human astrocytes responded to both ATP and glutamate stimulation with increased intracellular calcium concentrations (FIG. 4). The percentage of cells responding to the stimuli and the level of response depended the concentration of ATP and glutamate (30 nM-670 µM) (FIGS. 4 A and B). Intriguingly, postnatal human astrocytes responded to ATP and glutamate with distinct temporal patterns. Independent of concentration, glutamate stimulation consistently produced a synchronous 'all or none' rise in intracellular calcium levels among nearly every astrocyte that then quickly decreased (within 10 seconds) to baseline levels (FIGS. 4 C and D). In contrast, the onset of calcium response to ATP stimulation was asynchronous among the astrocytes in the imaging chamber. After the initial calcium elevation, some cells exhibited oscillatory fluctuations in calcium concentrations that lasted for minutes after initial ATP stimulation (FIGS. 4 C and D). In summary, human astrocytes exhibited a synchronous non-oscillatory response to glutamate and an asynchronous oscillatory response to ATP stimulation.

Transcriptome profiling of acutely purified human neurons, astrocytes, oligodendrocytes, microglia, and endothelial cells. The human brain is composed of neurons, glia (astrocytes, oligodendrocytes, microglia) and vascular cells. Each of these cell types have a distinct role to play in the nervous system, and each can be characterized by a unique molecular repertoire necessary for cell-specific functions. Constructing a transcriptome database of purified cell types from human brains could help to identify cell type specific markers, reveal novel cell type specific functions, and find receptors and ligands that various cell types of the brain use to communicate with each other.

To construct a transcriptome database of purified human neurons, astrocytes, oligodendrocytes, microglia, and endothelial cells, we acutely isolated each cell type by immunopanning (FIG. 1), extracted RNA, performed RNA-seq and obtained pair-end 150 bp reads. To assess the purity of our immunopanning-isolated cell samples, we probed the transcriptome data for expression of well-known cell-specific genes for astrocytes (e.g. Gfap, Aldh1l1, Sox9, Aqp4), neurons (e.g. Vglu1, Stmn2, Syt1, Syn1), oligodendrocytes (e.g. Plp1, Mog, Sox10, Mbp), microglia/macrophages (e.g. C1qa, Cx3cr1, Ccl3, Tnt), and endothelial cells (e.g. Cldn5, Eltd1, Itm2a, Esam) (FIGS. 5 A and B). The expression of these classical cell-specific markers each demonstrated definitive cell type selectivity in their corresponding cell types with undetectable or low level of expression by other cell populations not known to express these markers (FIGS. 5 A and B). These data helped to confirm the purity of the various isolated cell types.

Figure 5B:
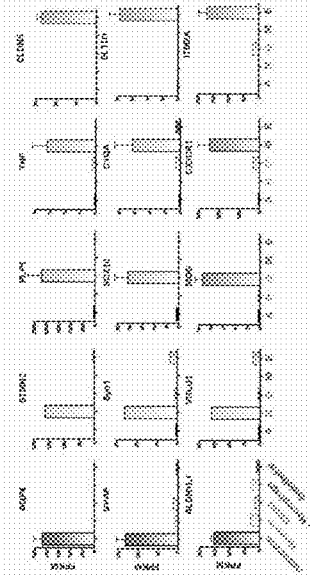
FIG. 5B. Representative examples of the expression of cell type-specific genes by acutely purified cell samples. FPKM: fragments per kilobase of transcript sequence per million mapped fragments.
Figure 5A:
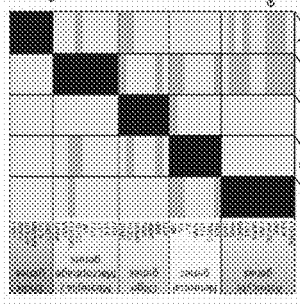
FIG. 5A. Expression of classic cell type-specific genes by acutely purified human neurons, astrocytes, oligodendrocytes, microglia/macrophages, and endothelial cells. Data represent standard deviation from mean across rows.
Figure 5E:
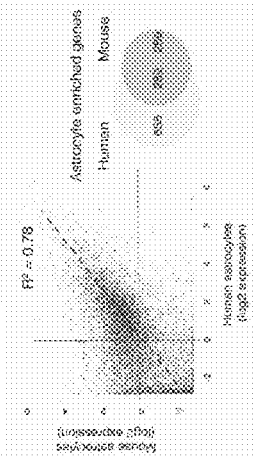
FIG. 5E. Scatterplot of human and mouse astrocyte gene expression. $R^2$ represents the square of Spearman correlation coefficiency. Venn diagram indicates the number of astrocyte enriched genes (>4 fold, FPKM>5) for human and mouse astrocytes.
Figure 5D:
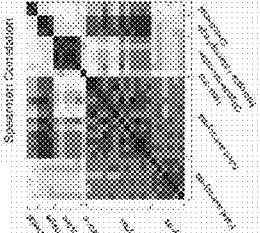
FIG. 5C. Expression of proliferative and mature markers in fetal and adult astrocyte samples FIG. 5D. Spearman correlation between all fetal and adult samples.
FIG. 5F. In situ hybridization stainings performed on temporal lobe cortices from healthy patients (separate source from the RNAseq samples). Unique probes were designed against LRRC3B and GPR98 (cyan) and sections were counterstained against the astrocyte specific transcription factor, Sox9. Scale bars: 100 μm zoomed out, 50 μm insets. See also Table 2.
Figure 5C:
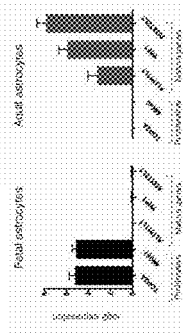
Figure 5F:
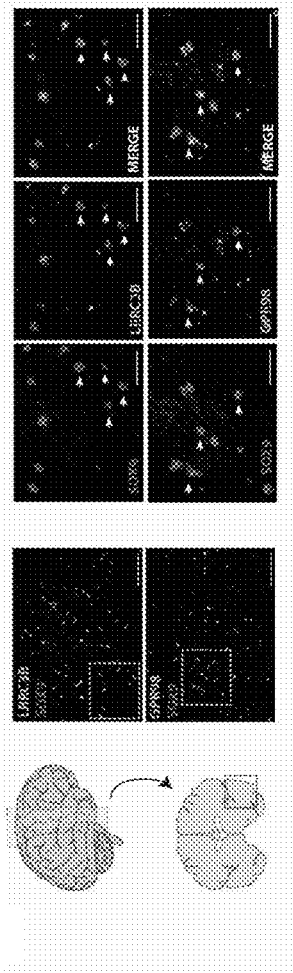

Unlike inbred laboratory mice, human patients have diverse genetic backgrounds and distinct environmental influences. We wondered whether the vast individual differences between human patients might significantly affect the construction of cell type transcriptome dataset. Therefore, we examined the correlation between samples obtained from different patients (n=12, age range: 8-63 years) and found high correlations between cell type replicates and low correlation among samples of differing cell types (FIG. 5C). Additionally, we performed unsupervised hierarchical clustering and found that samples belonging to the same cell type clustered closely together (FIG. 5D). These results indicate that the transcriptome differences between cell types are sufficiently consistent that they do not become obscured by individual genetic and/or environmental variations between patients.

We next wanted to assess whether human and mouse astrocytes share similar gene expression profiles. Since existing RNAseq data from mouse astrocyte was collected from sorting genetic lines, we collected new mouse astrocyte samples using an identical procedure as our human astrocytes—including the use of the same monoclonal HepaCAM antibody for immunopanning. We then compared the RNA-seq based transcriptomes of human and mouse astrocytes. We found significant overlap in the genes expressed by astrocytes from humans and mice, including all of the classic astrocyte-specific genes (e.g. Gfap, Aldh1l1, GluI, Aqp4, Slc1a2, and Slc1a3) (FIG. 5 E). The top 40 astrocyte-enriched genes shared by humans and mice and the top 40 human astrocyte-specific genes are listed in Table 1. These human astrocyte-specific genes (e.g. Wif1, Gpr98, Ryr3, and Mrvi1) provide insight into the unique properties of human astrocytes and the contribution of astrocytes to the superior cognitive abilities of humans compared with other species.

Reactive changes of human astrocytes in neurological disorders. Astrocytes undergo reactive astrogliosis in response to injury or disease, which involve phenotypic changes including proliferation, hypertrophy, and the secretion of inflammatory cytokines and chemokines. Since the physiology and function of quiescent and reactive astrocytes are distinctly dissimilar, an understanding of gene expression from both populations is critical for interpreting the role of astrocytes in both health and disease. Previous methods of enriching human astrocytes in serum-based cultures involve long-term exposure to a nonphysiologic environment. Serum exposure in culture has been shown to induce irreversible reactive changes in astrocytes and resting astrocytes in vivo are never exposed to serum except after blood-brain-barrier breakdown. Furthermore, astrocytes grown in vitro via serum-selection methods demonstrate unusual polygonal fibroblast-like morphologies that are not present in vivo, whereas our acutely purified astrocytes grown in serum-free medium exhibit extensive process bearing morphologies (FIGS. 1 and 3). To test whether exposure to serum could elicit morphological changes in what we suspected were quiescent astrocytes, we added serum to our cultures of immunopanned human astrocytes and quickly noted a transition from a process-bearing morphology to the polygonal fibroblast-like morphology typically found in serum-cultured cells (FIG. 3A).

Figure 6A:
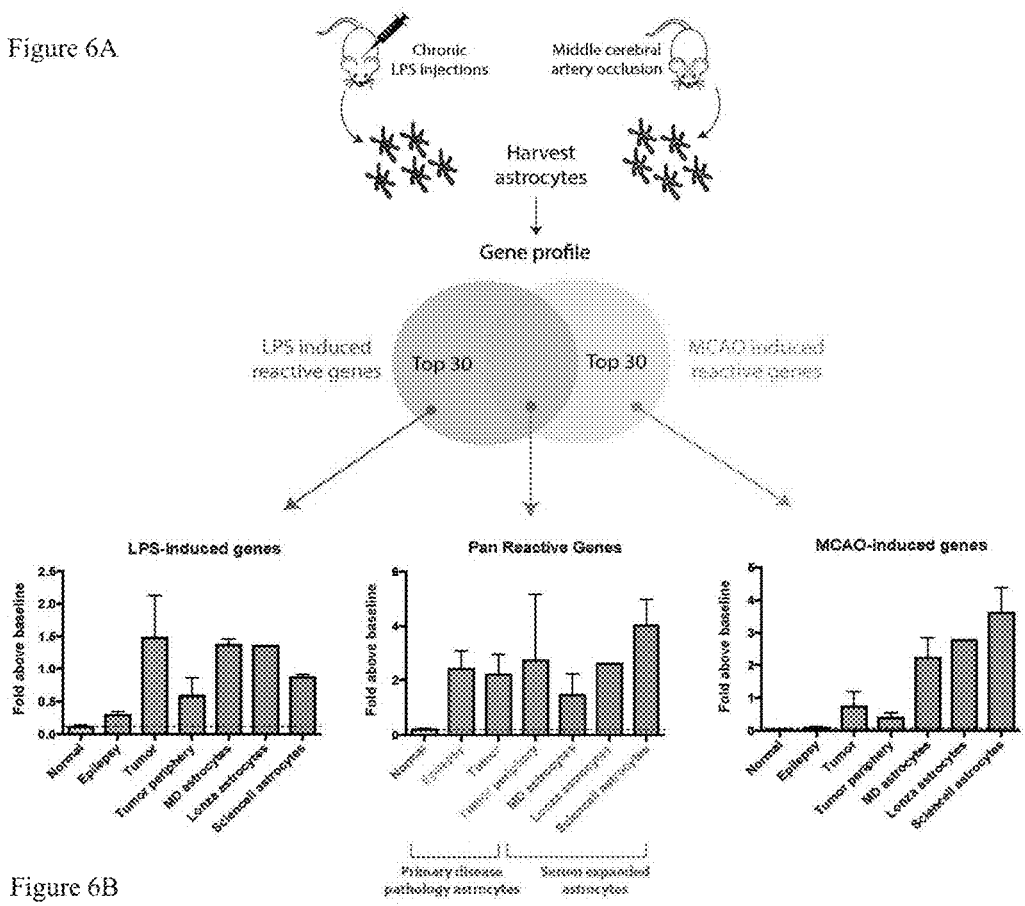
FIG. 6A-6B. Acutely purified human astrocytes display resting gene profiles.
Figure 6B:
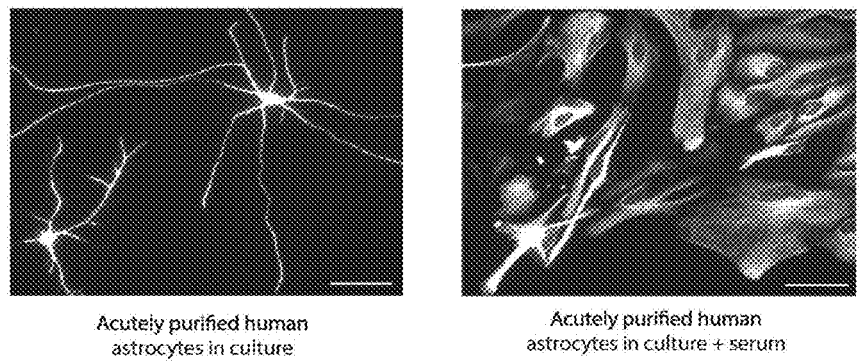
Figure 7:
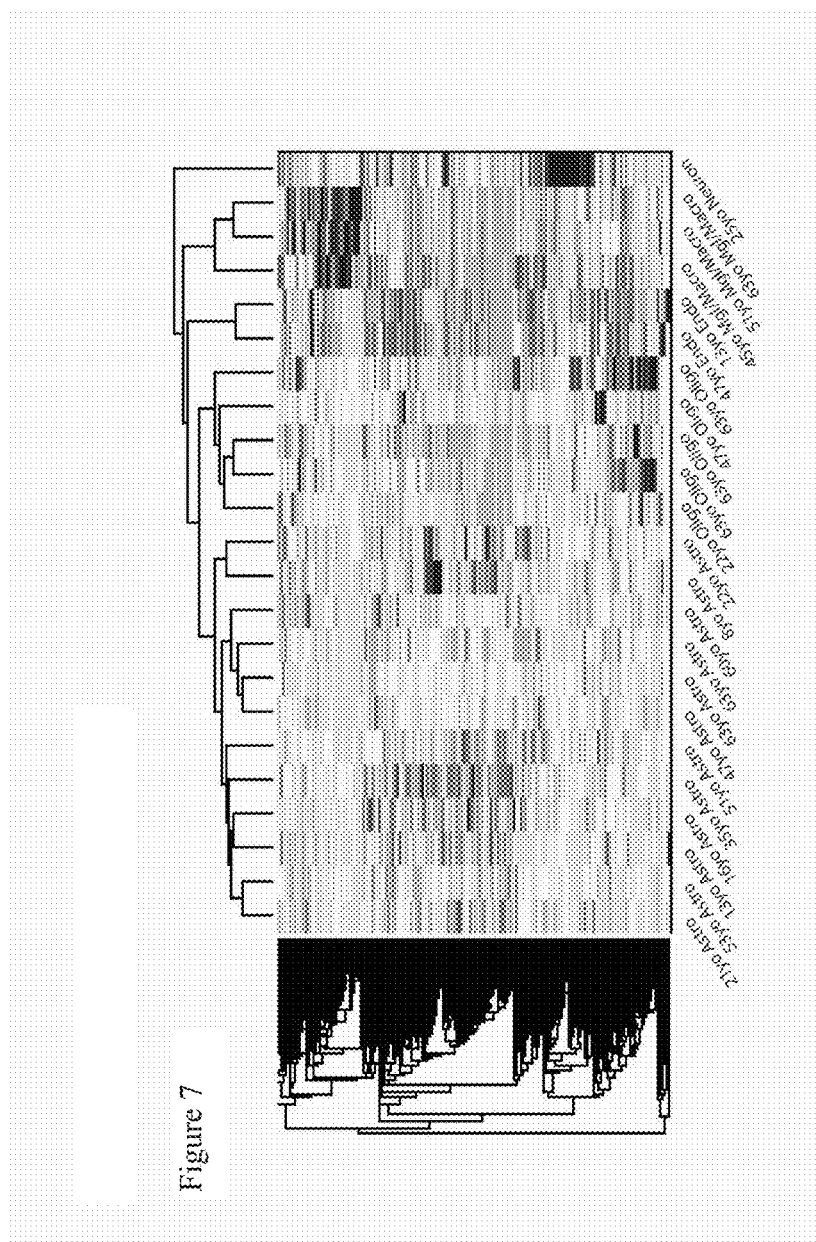
FIG. 7. Hierarchical clustering of gene expression of acutely purified postnatal human samples. Astro, astrocyte. Oligo, oligodendrocytes. Endo, endothelial cells. MgI/Maco, microglia/macrophage.

To examine whether the transcriptome profiles of acutely purified human astrocytes more closely resembled resting or reactive astrocytes, we probed the RNAseq dataset for reactive astrocyte genes. Previous reports of mouse reactive astrocytes have described two distinct types of reactive phenotypes, a bacterial lipopolysaccharide (LPS) infection induced "A1" phenotype, which includes up-regulation of genes involved in inflammatory responses, and an ischemia induced "A2" phenotype, which includes up-regulation of genes involved in tissue repair. We next cross-referenced the top 30 genes induced by ischemia alone, LPS alone, or both injury models with our acutely purified human astrocytes (FIG. 6). We found low expression of these reactive astrocyte markers in acutely purified human astrocytes from (representative examples are shown in FIGS. 6A-C and average expressions are shown in FIGS. 6D-F). In contrast, we found that human astrocytes obtained from serum selection methods (MD astrocytes in FIG. 6) (Mense et al., 2006), including those from two commercial sources, Lonza and Sciencell (Lonza astrocytes and Sciencell astrocytes in FIG. 6), expressed high levels of these reactive astrocyte markers.

Do human astrocytes undergo reactive changes in neurological diseases? Numerous postmortem immunofluorescence studies of patients with a variety of neurological conditions have demonstrated up-regulation of a single reactive astrocyte marker, GFAP, but a transcriptome level examination of reactive changes in human astrocytes has not yet been performed. To supplement our library of healthy human astrocytes, we acutely purified astrocytes from brain samples taken from regions involved in epilepsy and glioblastoma (core, MRI contrast-enhancing regions as well as peripheral non contrast-enhancing regions). We then performed RNA-seq to compare transcriptomes of disease-affected astrocytes with healthy human astrocytes, with a particular focus on the expression of the previously identified reactive astrocyte markers. Much like in serum-cultured astrocytes, we found significant increases in the expression of the reactive astrocyte genes in disease-affected astrocytes (FIG. 6). The epilepsy and tumor derived human astrocytes induced comparable fold changes in their reactive astrocyte gene expression profiles as ischemia and LPS injuries did in mice (Average fold change in epilepsy in humans, $3.4\pm0.7$; tumor core in humans, $29\pm16$; tumor peripheral in humans, $5.6\pm1.0$, ischemia in mice, $18.0\pm3.0$, LPS in mice, $12.4\pm4.3$.). Interestingly, astrocytes that were purified from epileptic regions expressed higher levels of inflammatory reactive astrocyte (A1) genes than ischemic reactive astrocyte (A2) genes (average normalized expression of A1 genes: $0.29\pm0.02$; A2 genes: $0.09\pm0.03$. $p<0.05$), suggesting that astrocytes may have more pro-inflammatory function than tissue remodeling and repair function in epileptic regions. These results demonstrate that human astrocytes undergo robust reactive changes in epilepsy and glioma.

Discussion

We have developed a method to acutely purify human astrocytes and established serum-free culture conditions to grow human astrocytes in vitro. Using this method, we demonstrated that human astrocytes share similar functions as rodent astrocytes in promoting neuron survival, synapse formation, and synapse-engulfment. We also found that human astrocytes retain their larger size in vitro and demonstrate distinct calcium response patterns to ATP and glutamate stimulation. We performed RNA-seq transcriptome profiling of purified human neurons, astrocytes, oligodendrocytes, microglia, and endothelial cells and established a database that serves as a road map for understanding cell type specific gene function in the human brain. By comparing human and mouse astrocyte transcriptome profiles, we found large numbers of genes shared by astrocytes of both species as well as a gene expression signature unique to human astrocytes. We further demonstrated that acutely purified human astrocytes from normal brain samples exhibit resting astrocyte gene expression profiles and that epilepsy and tumor robustly induce reactive changes in astrocytes.

The vast majority of drug candidates for neurological disorders succeed in rodent model studies but fail in human clinical trials. There is a strong need for human cell culture models for disease mechanism studies and drug testing. As astrocytes have been found to be key players in many neurological disorders, improvement of human astrocyte culture methods may lead to new discoveries in the treatment of neurological disorders. Previously developed serum-based culture methods generate human astrocytes that express reactive astrocyte genes and are already in a disease-like state. Therefore, it is difficult to identify additional disease-induced changes above the background reactive changes with these cells. The human astrocytes obtained by our acute purification method exhibit resting astrocyte transcriptome profiles, providing a baseline by which to compare changes in gene expression in disease vs. healthy brains. The proof-of-principle studies of changes induced by epilepsy and glioma demonstrates the value of the new purification method.

Although neuronal heterogeneity is widely recognized and studied, we understand little about the heterogeneity of astrocytes in mice or humans. From immunohistological observations of human brain tissue, Nedergaard and colleagues discovered that human astrocytes exhibit greater morphological heterogeneity than rodent astrocytes. The extent of the molecular and functional heterogeneity of human astrocytes that exists among differing CNS regions remains relatively unknown. Although the majority of the samples we used in this study were taken from temporal lobe cortex, we found that our purification method works well on astrocytes from other brain regions like hippocampus and cerebellum. This acute purification method provides a new avenue for studying regional astrocyte heterogeneity in the human CNS.

Functional and molecular similarities between human and rodent astrocytes. Considering that the majority of our understanding of astrocyte function derives from studies in rodent models, it is important to examine the extent of functional similarities between human and rodent astrocytes. We found that primary human astrocytes share many core functions with rodent astrocytes, which include effects on neuron survival, synapse formation and engulfment. The efficiency of human astrocytes to promote synapse formation and to engulf synaptosomes is comparable to rodent astrocytes as determined by the in vitro assays we performed.

At the molecular level, our transcriptome comparison of human and rodent astrocytes also revealed substantial similarities. For example, human astrocytes express high levels of glutamate transporter genes (Slc1a2 and Slc1a3) and glutamine synthetase gene (GluI), suggesting that human astrocytes likely uptake glutamate from synaptic clefts and convert it to glutamine much like rodent astrocytes. Human astrocytes express high levels of genes encoding the water channel Aqp4 and the inward rectifying potassium channel Kir4.1, suggesting that human astrocytes likely also partake in canonical astrocyte roles like water and potassium homeostasis.

Unique properties of human astrocytes. The expansion of the primate cortex throughout the course of evolution raises questions about the molecular mechanisms underlying increased neurogenesis and astrocytogenesis during development. Recent work has provided mechanistic insights about the cellular and molecular mechanisms that contribute to the expansion of neuronal populations in the human CNS, including the appearance of outer radial glia cells in the outer subventricular zone and the presence of primate-specific signaling pathways like PDGFD and ARHGAP11B. Despite this progress, we still understand little about the mechanisms that promote astrocyte generation in humans. Our transcriptome dataset of human astrocytes, particularly at the fetal stage when astrocytes are actively being generated, will provide molecular candidates to understand this process.

A question of great interest in biology is to understand why humans have superior cognitive abilities compared with other species. Humans have enormously better abilities to learn and remember compared with mice. Since synapse formation and elimination are key structural changes in learning and memory and astrocytes are critical for synapse formation and elimination, it is important to understand whether unique properties of human astrocytes contribute to the cognitive differences between human and mice. Human and mouse brains also differ tremendously in the duration of development and lifespan. Neural circuit wiring happens over years in humans and only weeks in mice. Human brains are built to last for decades and must defend themselves against more oxidative damages, injuries, and diseases than mouse brains. Determining which unique properties of human astrocytes contribute to the prolonged plasticity window and the long-lasting protection against injuries and diseases in human brains is of great interest.

We started to characterize the unique properties of human astrocytes by performing unbiased comparison of the transcriptome of human and mouse astrocytes. We found a number of genes expressed by human astrocytes but not by mouse astrocytes. Some of these genes are offering intriguing possibilities in understanding the physiological and functional properties unique to human astrocytes.

Nedergaard and colleagues found faster propagation of calcium transients in the processes of human astrocytes compared with rodent astrocytes. The molecular mechanism underlying such difference is unknown. We found that ryanodine receptor 3 (Ryr3) is highly expressed by human astrocytes but not by rodent astrocytes. Ryr3 is a calcium permeable ion channel located on the membrane of endoplasmic reticulum (ER) and sarcoplasmic reticulum, where calcium is stored inside cells. It is activated by elevation of cytoplasmic calcium concentration and releases calcium from the internal store in a process called "calcium activated calcium release" in muscle cells. The unique presence of Ryr3 in human astrocytes might amplify elevation of intracellular calcium concentration and allow saltatory propagation of calcium transients along astrocyte processes by releasing calcium from spatially discrete ER compartments. Additional human astrocyte-specific molecules, for example orphan G-protein coupled receptor, Gpr98, might provide novel insight into cell-cell interactions in human brains. The genes expressed by human temporal lobe cortex astrocytes but not by mouse astrocytes from entire cortices that we described above should be unique to human astrocytes.

As the evidence accumulates for the importance of astrocytes in brain health and disease, the purification method and transcriptome dataset presented here will be an invaluable resource for investigating the biology of human astrocytes and searching for new treatment approaches for neurological disorders.

Experimental Procedures

Human tissue. Human brain tissue was obtained with informed consent under a Stanford University Institutional Review Board approved protocol. Postnatal human brain tissue was obtained from surgeries for treating epilepsy and tumors. All the experiments described in this study, except the reactive astrocyte gene induction studies (FIG. 6, epilepsy, tumor, and tumor peripheral data), were performed with by-and-large normal temporal lobe cortex resected in order to access deeper hippocampus areas involved in epilepsy. The cortical tissue was determined as normal by electroencephalogram (EEG) and magnetic resonance imaging (MRI). For assessment of reactive astrocyte gene expression we used sclerotic hippocampus specimens involved in epileptic foci and cortical specimens from glioblastoma core and peripheral regions, defined as contrast enhancing and non-contrast enhancing regions, respectively. Tissue was immersed in 4° C. Neurobasal medium (21103-049; Gibco) and transferred to the lab for tissue dissociation within 1 hour after resection. Fetal human brain tissue was obtained following elective pregnancy termination. Tissue was immersed in 4° C. RPMI medium (12633-012; Life Technologies) and transferred to the lab for tissue dissociation within 5 hours after the procedure.

Vertebrate animals. All procedures involving animals were conducted in conformity with Stanford University guidelines that are in compliance with national and state laws and policies.

Purification of postnatal human astrocytes, neurons, oligodendrocytes, microglia/macrophages, and endothelial cells. We dissected out grey matter from postnatal human brain specimens and removed meninges and blood clots, and then chopped the tissue into pieces <1 mm$^3$. We then incubated the tissue in 20 unit/ml papain at 34° C. for 100 minutes and washed with a protease inhibitor stock solution. We then gently triturated the tissue with 5 ml serological pipettes in the protease inhibitor stock solution and before spinning the cell suspension through a layer of protease inhibitor stock solution. We resuspended the cells in PBS with BSA and DNase and passed it through a Nitex filter to remove cell clumps. We then added the single cell suspension to a series of plastic petri dish pre-coated with cell type specific antibodies and incubated for 10-30 minutes each at room temperature (see specific protocol in Supplemental Information). Unbound cells were transferred to the subsequent petri dish while the dish with bound cells was rinsed 8 times with about 20 ml of PBS each time to wash away loosely bound contaminating cell types. The antibodies used include anti-CD45 to capture microglia/macrophages, anti-GalC hybridoma supernatant to harvest oligodendrocytes, anti-O4 hybridoma to harvest oligodendrocytes precursor cells, anti-Thy1 (CD90) to harvest neurons, anti-HepaCAM to harvest astrocytes, and finally *Banderiaea simplicifolia* lectin 1 (BSL-1) to harvest endothelial cells. For RNAseq, cell samples were scraped off the panning dish directly with Qiazol reagent (Qiagen). For cell culture and in vitro experiments, astrocytes bound to the anti-HepaCAM antibody coated dishes were incubated in a trypsin solution and incubated at 37° C. for 5-10 minutes and gently squirted off the plate. We then spun down the astrocytes and plated them on poly-D-lysine coated plastic coverslips in a Neurobasal-DMEM based serum-free medium. We replaced half of the volume with fresh medium every 3-4 days to maintain the cultures.

Purification of fetal human astrocytes and neurons. Fetal human astrocytes and neurons were purified in a similar protocol to the above-mentioned procedure with the following modifications: 7.5 unit/ml papain was used and the papain digestion time was shortened to 45 minutes. After obtaining a single cell suspension, the suspension was incubated in a 34° C. waterbath for recovery of cell surface antigens digested by papain. Only the following three panning dishes were used: one coated with anti-CD45 to harvest and deplete microglia/macrophages, one coated with anti-Thy1 to harvest and deplete neurons, and one coated with anti-HepaCAM to harvest astrocytes. Although we routinely obtained >95% pure postnatal human astrocytes, the fetal astrocytes obtained by immunopanning have slightly lower purity and contain a small population of TBR2 positive intermediate progenitors that give rise to neurons in vitro.

Purification of adult mouse astrocytes. For comparison of human and mouse astrocyte transcriptomes, we used 1, 4, 7, and 9 month-old C57BL6 mice, harvested grey matter from the whole cortex, and purified astrocytes with the identical protocol for postnatal human astrocytes.

Immunocytochemistry. Cultured cells were fixed with 4% PFA for 10 minutes at room temperature, permeablized and blocked with 10% goat serum with 0.2% Triton-X100. The following primary antibodies were used: chicken anti-GFAP (1:1000, Covance PCK-591P), rabbit anti-GFAP (1:1000, Dako Z0334), mouse anti-TuJ1 (1:1000, Sigma T8660), rabbit anti-TBR2 (1:2000, Abcam Ab23345), mouse anti-bassoon (1:500, Stressgen) and rat anti-Homer (1:1000, Chemicon). The appropriate secondary antibodies conjugated with Alexa fluorophores (Invitrogen) were used. The stained samples were mounted in VectorShield with DAPI (Vector Labs, H1200) to stain the nuclei of all cells. Images were acquired using a Zeiss Axiolmager fluorescence microscope.

Neuron survival assay. We purified human fetal neurons with anti-Thy1 antibody and astrocytes with anti-HepaCAM antibody as described above. Neurons were plated at 10,000 cells per well on PDL-coated plastic coverslips in 24 well cell culture plates in serum-free medium containing BDNF and CNTF (see medium composition in Supplemental Information). Astrocytes were plated on PDL-coated cell culture inserts with 1 μm diameter pores (Corning, 08-771-9) in serum-free medium containing HBEGF (Supplemental Information). Neuron survival was determined according to manufacturer's instructions with the Live/dead Viability/Cytotoxicity kit (Invitrogen, L3224) at 5 div.

Synapse formation assay. We purified RGCs by sequential immunopanning to greater than 99% purity from P5-P7 Sprague-Dawley rats (Charles River) and cultured in serum-free medium containing BDNF and CNTF on PDL-laminin coated glass coverslips at 75,000 cells per well as previously described (Winzeler and Wang, 2013). Human astrocytes were plated on inserts at 100,000-150,000 cells per insert and co-cultured with RGCs for 14-17 days. For quantification of structural synapses, RGCs were fixed and stained with antibodies against presynaptic marker Bassoon and postsynaptic marker Homer as described in the immunocytochemistry section above. Images were acquired by a 63× lense on a Zeiss Axiolmager fluorescence microscope. Imaging fields were randomly selected by viewing with the DAPI channel to avoid biased selection of regions with dense or sparse synapses. Ten images each containing 1-6 cells were acquired from each coverslip and 2-3 coverslips per condition were imaged. Synapse number and size were quantified by a custom-written Matlab program (available upon request), which performs image thresholding, rolling ball background subtraction, puncta size selection, and recognizes colocalized signal from the Homer and Bassoon channels as synapses. The same thresholding settings were used for all images from each batch of experiment.

Electrophysiology. Whole-cell patch-clamp recordings from cultured RGC neurons were performed at room temperature in an isotonic saline solution (in mM: NaCl 125, NaHCO$_3$ 25, KCl 2.5, NaH$_2$PO$_4$ 1.25, glucose 25, MgCl$_2$ 1, CaCl$_2$ 2). Patch electrodes with resistances of 2.5-3.5 MΩ were pulled from thick-walled borosilicate glass capillaries and were filled with an internal solution containing (in mM) potassium gluconate 130, NaCl 4, EGTA 5, CaCl$_2$ 0.5, 10 HEPES, MgATP 4, Na$_2$GTP 0.5 (pH 7.2 with KOH). Miniature excitatory postsynaptic currents (mEPSCs) were recorded in TTX (1 μM, Alomone) from a holding potential of −70 mV. Series resistance was monitored throughout the recording and was <20 MO. Data were sampled at 50 kHz and filtered at 1 kHz using pClamp 9.2, and offline analysis of mEPSCs was performed using Clampfit 10.3 (Molecular Devices).

Synaptosome engulfment assay. Synaptosome purification and in vitro engulfment assays were performed as previously described. Briefly, synaptosomes were purified by percoll gradient from adult mouse brains and incubated with pHrodo Red, succinimidyl ester (Life Technologogies P36600). Human fetal and postnatal astrocytes were purified as above and grown for 7 days in vitro. After 7 days, the medium was replaced with either fresh medium supplemented with 5% serum (control), conditioned medium with synaptosomes, or fresh medium with synaptosomes and 5% serum. After incubating the astrocytes at 37° C. for 3 hours, the cells were washed twice with PBS and lifted by trypsin digestion and gentle trituration. The cell suspension was then analyzed for pHrodoRed fluorescence with a BD Aria II sorter or LSR analyzer.

Morphology measurements. Human postnatal astrocytes were purified as above and rat postnatal astrocytes were purified as previously described and plated to reach similar final density in the same growth medium. The cells were fixed and stained with anti-GFAP antibody at 5-6 div. Branches were traced with NIH ImageJ and the length and number of branches were quantified.

Calcium imaging. Purified human astrocytes were plated at 100,000 cells/imaging chamber (MatTek, P35GC-1.0-14-C) coated with poly-d-lysine. Cells were grown for at least 5 days before imaging. Cells were incubated for 15 minutes with 2 µM Fluo 4 AM (Invitrogen, F-14201) and then washed 3 times with PBS and replaced with 1.5 ml of growth medium per chamber. The cells were then let to recover from mechanical stimulation for 3 minutes and then imaged in a humidified, temperature-controlled chamber with a 40× oil objective. Images were taken at 0.7 s intervals and analyzed with ImageJ.

RNA-seq library construction and sequencing. Total RNA was extracted using the miRNeasy kit (Qiagen) under the protocols of the manufacturer. The quality was assessed by Bioanalyzer. Samples with RNA integrity number higher than 8 were used for library construction. We used the Ovation® RNA-seq system V2 (Nugen 7102) to perform first and second-strand cDNA synthesis and SPIA amplification following the manufacturer's instructions, and fragmented cDNA with a sonicator (Covaris S2) using the following parameter: duty cycle 10%, Intensity 5, Cycles/burst 100, time 5 minutes. We then used the Next Ultra RNAseq library prep kit for Illumina (NEB E7530) and NEBNext® multiplex oligos for Illumina® (NEB E7335 E7500) to perform end repair, adaptor ligation, and 5-6 cycles of PCR enrichment according to manufacturer's instructions. The quality of the libraries were then assessed by bioanalyzer and qPCR and high quality libraries were sequenced by the Illumina NextSeq sequencer to obtain 150 bp pair-end reads.

RNA-seq read mapping, transcript assembly, and expression level estimation. We analyzed RNA-seq reads with the Galaxy web-platform. The FASTQ files were first groomed using the FASTQ groomer and then mapped using TopHat2, which invokes Bowtie as an internal read mapper. The paired end option was selected and human genome version 19 (hg19) was used as the reference genome. We then ran Cufflinks to assemble transcripts and estimate expression level as fragments per kilobase of transcript sequence per million mapped fragments (FPKM).

Reactive astrocyte gene expression analysis. Reactive astrocyte genes were identified from the Zamanian mouse reactive astrocyte dataset using 2-fold induction as the threshold. Genes induced by both ischemia and LPS, only by ischemia, and only by LPS were ranked by fold induction and the 30 genes with highest fold induction from each of the three categories were used as reactive astrocyte marker genes. The expression level of each reactive astrocyte gene from our human data and from the Zamanian mouse dataset were all normalized to the expression level of the housekeeping gene GAPDH under each respective condition to minimize differences introduced by different transcriptome profiling platforms (RNA-seq for our human data and microarray for the Zamanian mouse reactive astrocyte data). Normalized expression of each reactive astrocyte gene from each of the human astrocyte samples was then calculated as $$\frac{\text{Expression in human astrocyte sample} - \text{Expression in mouse resting astrocyte}}{\text{Expression in mouse reactive astrocyte} - \text{Expression in mouse resting astrocyte}}$$

Detailed protocol for the purification of human astrocytes
Day Before
Prepare Panning Dishes:
Set up panning plates in 15 cm petri dishes. 15 ml of 50 mM Tris-HCl pH 9.5 per dish.
1×CD45 plate: 60 µl anti-rat IgG
3× GalC plate: 60 µl anti-mouse IgG
2× O4 plate: 60 ul anti-mouse IgM □-chain specific
1× Thy1 plate: 60 µl anti-mouse IgG
1× HepaCAM plate: 60 µl anti-mouse IgG Prepare coverslips (this can also be done on the day of prep): Wash coverslips once with sterile distilled water, transfer coverslips into 24 well plates, add 10 ug/ml poly-D-lysine to each well, incubate at room temperature for 30 minutes, wash 3 times with water, and aspirate residual water to dry.
Day of Prep
Solutions to Prepare:
*20 ml×1 enzyme stock+Papain (400 units for postnatal and 150 units for fetal tissue)+0.0032-0.0040 g L-cysteine
**21 ml×2 inhibitor stock+1.5 ml Low Ovo+100 µl DNase
**10 ml×1 inhibitor stock+2 ml High Ovo+20 µl DNase
***60 ml×1 0.2% BSA: 57 ml dPBS+3 ml 4% BSA+60 µl DNase
***50 ml×1 0.02% BSA: 45 ml dPBS+5 ml of 0.2% BSA+50 µl DNase Aliquot 20 ml of enzyme stock* into a 50 ml Falcon tube, break 2 ml pipette, attach filter on top, bubble $CO_2$ through until solution turns from red to orange, and put into 34□C water bath.

Aliquot and bubble 2×21 ml and 1×10 ml inhibitor stock** as in 1.

Wash each panning dish with PBS 3× then add the following antibodies: 20 µl CD45 in 12 ml of 0.2% BSA***, 4 ml GalC in 8 ml of 0.2% BSA, 4 ml O4 in 8 ml of 0.2% BSA, 20 ul Thy1 in 12 ml of 0.2% BSA, and 15 ul HepaCAM in 12 ml of 0.2% BSA.

Add papain to enzyme stock* bubbled with $CO_2$ and add 0.0036-0.0042 g of L-cysteine. Warm up solution mixture in 34□C water bath at least 15 minutes before digestion.

Dissect brains in dPBS in 6 cm petri dishes, cut out grey matter, remove meninges and blood clots, use No. 10 scalpel blade to chop brains into <1 mm³ pieces. Put ~0.5 g of tissue into each 6 cm petri dish and use multiple petri dishes for digestion if there are more than 0.5 g of tissue.

Use 0.22 mm filter to filter and discard 2 ml of enzyme stock, then filter 10 ml into each petri dish containing finely chopped brain pieces. Add 100 µl DNase to each petri dish and swirl dish to mix.

Papain digestion: Put the petri dish on a 34 °C heat block, drill a ~0.5 cm diameter hole into the lid of the 6 cm petri dish with heated forceps, attach tubule from a $CO_2$ tank to a 0.22 mm filter and put the filter tip into the hole so $CO_2$ flows over the enzyme stock solution with brain pieces. Shake the petri dish every 15 minutes. Digest for 100 minutes for postnatal tissue and 45 minutes for fetal tissue.

Equilibrate 20 ml of 30% FCS and 8 ml of EBSS in the incubator

After digestion, put digested brains into a Universal tube, wait for tissue to settle, aspirate supernatant, add 4.5 ml of Low Ovo to cells to wash, wait for tissue to settle, repeat for a total of 4 washes.

Triturate. Add 4 ml of Low Ovo into the Universal tube, suck up brain and Low Ovo solution with a 5 ml serological pipette quickly and release quickly, repeat for 20-40 times. Be careful not to introduce bubbles. Do not lift 5 ml pipette out of solution during solution to minimize introduction of air into the solution. Low Ovo will become cloudy, let brain chunks settle. Transfer single cells with a 1 ml pipette to a Falcon tube, this is the cloudy solution on top of the chunks. Add to 4 ml of Low Ovo to the Universal tube and repeat trituration. Grey matter will dissociate faster than white matter. Stop trituration when all the visible brain pieces left are white matter (white color).

Count cells by diluting it 1:1 with Trypan Blue. For postnatal human tissue, expect 2M brain cells from each gram of brain tissue. There will be lots of debris, plenty of red blood cells, and sparse brain cells. Do not count the red blood cells (they are small and bright). Expect much higher yield and no debris from fetal brain tissue.

Carefully use a 10 ml pipette to layer 10 ml of High Ovo under the single cell suspension. This should lead to a clear layer of liquid beneath a cloudy cell suspension.

Spin cells down through High Ovo at 100 g for 5 mins.

Aspirate liquid, one should see a pellet of cells at bottom of Falcon tube.

Resuspend cell pellet gently with 9 ml of 0.02% BSA***

Filter cell suspension through Nitex mesh to remove chunks.

Wash each panning dishes with 3× dPBS immediately before use.

Add cell suspension to CD45 plate and incubate at room temperature for 15 minutes.

Examine the panning dish under a DIC microscope. If cells start to cluster, triturate gently with a 10 ml serological pipette. Transfer the cells to the next panning plate either after the suggested time in this protocol or when visual examination of the plate indicates there are lots of cells stuck.

Shake the CD45 plate and transfer cell suspension to a GalC plate. Then use 1 ml 0.02% BSA to wash the CD45 plate and collect the 1 ml of solution from the plate and add to the GalC plate. Incubate for 10 minutes.

Transfer to the second GalC plate.
Transfer to the third GalC plate.
Transfer to an O4 plate.
Transfer to the second O4 plate.
Transfer to the Thy1 plate.
Transfer to the HepaCAM plate.

Postnatal tissue: for harvesting cell for RNA-seq or any other experiment that requires maximum purity, go through all the panning steps as described above. For harvesting cells for cell culture, perform a shortened panning procedure to ensure maximum survival. Pass the cells through 2 GalC plates and then to the HepaCAM plate. Expect to see myelin debris on the HepaCAM plate. However, myelin debris will not stick to PDL-coated coverslips. Change medium at 1 div to wash away floating myelin debris. Fetal tissue: perform a shortened panning procedure. Pass the cells through CD45, Thy1, and HepaCAM plates.

Wash positive selection plate, ~8 times or until floating contaminating cells are gone with dPBS. For RNA-seq, scrape cells off with Qiazol reagent (Qiagen). For cell culture, go to the next step.

Add 200 units of trypsin to 8 ml of equilibrated EBSS, incubate at 37°C for 3-15 minutes. Since the activity of different lots of trypsin can vary, it is important to determine the duration of trypsin digestion empirically. Take the plate out of the incubator after 3 minutes, tap side of the plate, and look under the microscope. Incubate for longer if most cells are still stuck and stop the digestion if about half of the cells are dislodged.

Squirt gently around the plate with 10 ml of 30% FCS. Go through every part of the plate. Suck off dislodged cells and add to a 50 ml Falcon tube.

Add another 10 ml of 30% FCS to squirt if there are many cells left after the first round of squirting. Add cells to the Falcon tube.

Count cells.

Add 100 µl of DNase per 10 ml of solution and spin cells down at 130 g for 10 minutes.

Aspirate supernatant and resuspend cell pellet in growth media.

Pre-plate cells in 50 µl of media onto the center of coverslips. Gently transfer to the incubator, leave for 20 minutes, and carefully add on 450 µl growth medium per 24-well plate well.

Reagents
1× Earle's balanced salt solution (EBSS, Sigma E7510)
ACLAR plastic coverslips (Washed in 10% nitric acid over night on a shaker at room temperature and then in washed in water 5 times, 30 minute each, and in 75% ethanol once. Store in 75% ethanol.)
BDNF (Peprotech, 450-02)
Bovine serum albumin (Sigma, A4161)
Ciliary neurotrophic factor (CNTF, Peprotech 450-13)
Dulbecco's modified eagle medium (DMEM, Invitrogen, 11960-044)
Dulbecco's PBS (dPBS) Gibco
0.4% DNAse, 12,500 units/ml (Worthington, L5002007)
Fetal calf serum (FCS, Gibco, 10437-028)
Foskolin (Sigma F6886)
GalC hybridoma supernatant
Goat anti-mouse IgG+IgM (H+L) (Jackson ImmunoResearch, 115-005-044)
Goat anti-rat IgG (H+L) chain (Jackson ImmunoResearch, 112-005-167)
Goat ant-mouse IgM □-chain (Jackson ImmunoResearch, 115-005-02)
HBEGF (Sigma E4643)
Insulin (Sigma 1-6634)
L-cysteine hydrochloride monochloride (Sigma, C7880)
L-glutamine (Invitrogen, 25030-081)
Mouse anti HepaCAM (R&D systems, MAB4108)
N-Acetyl-L-cysteine (NAC, Sigma, A8199)
Neurobasal (Gibco, 21103-049)
Nitex mesh (Tetko Inc, HC3-20)
NS21-MAX (R&D systems, AR008)
O4 hybridoma supernatant (mouse IgM)

Papain (Worthington, LS 03126)
Penicillin/streptomycin (Invitrogen, 15140-122)
Poly-D-Lysine (Sigma, P6407)
Rat anti-mouse CD45 (BD Pharmingen, 550539)
SATO (See below)
Sodium Pyruvate (Invitrogen, 11360-070)
3,3',5-Triiodo-L-thyronine sodium salt (T3, Sigma T6397)
Trypsin 30,000 units/ml stock (Sigma, T9935)
Solutions Required
Enzyme Stock Solution

| Final Volume = 200 ml | | |
| --- | --- | --- |
| Component | Volume | Final Concentration |
| 10x EBSS | 20 ml | |
| 30% D(+)-Glucose | 2.4 ml | 0.46% |
| 1M NaHCO$_3$ | 5.2 ml | 26 mM |
| 50 mM EDTA | 2 ml | 0.5 mM |
| ddH$_2$O | 170.4 ml | |

Bring to 200 ml with ddH2O and filter through 0.22 µm filter
Inhibitor Stock Solution

| Final Volume = 500 ml | | |
| --- | --- | --- |
| Component | Volume | Final Concentration |
| 10x EBSS | 50 ml | |
| 30% D(+)-Glucose | 6 ml | 0.46% |
| 1M NaHCO$_3$ | 13 ml | 25 mM |
| ddH$_2$O | 431 ml | |

Bring to 500 ml with ddH2O and filter through 0.22 µm filter
Low Ovo (10×)
To 150 mL D-PBS, add 3 g BSA (Sigma A8806). Mix well. Add 3 g Trypsin inhibitor (Worthington L5003086) and mix to dissolve. Adjust pH to 7.4; requires the addition of approx. 1 mL of 1N NaOH. When completely dissolved bring to 200 mL with DPBS and filter through 0.22 µm filter. Make 1.0 mL aliquots and store at −20° C.
High Ovo (10×)
To 150 mL D-PBS add 6 g BSA (Sigma A8806). Add 6 g Trypsin inhibitor (Worthington L5003083) and mix to dissolve. Adjust pH to 7.4; requires the addition of at least 1.5 mL of 1N NaOH. If necessary, add NaOH until solution no longer too acidic. Bring to 200 mL with DPBS. When completely dissolved, filter through 0.22 µm filter. Make 1.0 mL aliquots and store at −20° C.
Sato (100×)
To Prepare:
Add the following to 80 mL Neurobasal medium: Final conc. 800 mg transferrin (Sigma T-1147); 100 µg/mL 800 mg BSA; 100 µg/mL 128 mg putrescine (Sigma P5780); 16 µg/mL 20 µl progesterone (Sigma P8783) (from stock: 2.5 mg in 100 µl EtOH) 60 ng/mL (0.2 µM) 800 µl sodium selenite (Sigma S5261) (4.0 mg+10 µl 1N NaOH in 10 mL NB) 40 ng/mL
*Do not reuse progesterone and Na selenite stocks; make fresh each time.
Mix well and filter through pre-rinsed 0.22 µm filter. Make 200 µl or 800 µl aliquots; store at −20° C.
Astrocyte Growth Media
50% Neurobasal
50% DMEM
100 units/ml of penicillin
100 µg/ml streptomycin
1 mM Sodium Pyruvate
2 mM L-glutamine
1×SATO
5 µg/ml NAC
5 ng/ml HBEGF
Neuron Growth Medium
For rat retinal ganglion cells and human fetal neurons
16 mL DMEM
4 mL dH2O
200 µL 0.5 mg/ml Insulin
200 µL 100 mM Pyruvate
200 µL 100× Penicillin/Streptomycin
200 µL 200 mM L-Glutamine
200 µL 100× Sato
200 µL 4 µg/ml Thyroxine (T3)
400 µL NS21-Max
20 µL 5 mg/ml NAC
Filter Sterilize
Immediately before use add 20 µL per 20 mL each: 4.2 mg/ml forskolin, BDNF, 10 µg/m; CNTF

TABLE 1

Top astrocyte-enriched genes shared by humans and mice and those unique to human astrocytes. Genes enriched in human astrocytes at least 5 fold over the average level in human neurons, oligodendrocytes, microglia/macrophages, and endothelial cells are included. Genes with FPKM values over 1 in mouse adult astrocytes are considered shared by both human and mouse astrocytes and genes with FPKM values under 1 in mouse adult astrocytes are considered unique to human astrocytes. Top 40 genes with highest expression in human astrocytes are listed.

| Top 40 Shared Human and Mouse Astrocyte Genes | Top 40 Human Specific Astrocyte Genes |
| --- | --- |
| SLC1A2 | WIF1 |
| SPARCL1 | ENO1 |
| SLC1A3 | GSTM2 |
| CPE | LRRC3B |
| GJA1 | HSD17B6 |
| ATP1B2 | FAM198B |
| AQP4 | MRVI1 |
| CLU | RYR3 |
| ALDOC | RGR |
| NTRK2 | ACBD7 |
| NDRG2 | STOX1 |
| ATP1A2 | NT5E |
| GLUD1 | GPR98 |
| AGXT2L1 | MOXD1 |
| FAM107A | AADAT |
| SCG3 | RERG |
| F3 | IL17RB |
| GFAP | CRB1 |
| DTNA | GPR75 |
| PPAP2B | NRG3 |
| GJB6 | ABCC9 |
| SLC4A4 | RANBP3L |
| BAALC | MMP28 |
| EZR | CACNB2 |
| NCAN | LMO3 |
| AGT | FBXL7 |
| SLC39A12 | TPD52L1 |
| MGST1 | ZFHX4 |
| CHRDL1 | BDH2 |
| LRIG1 | LGALS3 |
| PREX2 | ABLIM1 |
| HRSP12 | PRCP |
| TMEM47 | PLSCR4 |
| SOX9 | SRI |
| CLDN10 | ALDH2 |
| PPP1R3C | INTU |
| SLC25A18 | BBOX1 |
| ELOVL2 | PRKCA |

TABLE 1-continued

Top astrocyte-enriched genes shared by humans and mice and those unique to human astrocytes. Genes enriched in human astrocytes at least 5 fold over the average level in human neurons, oligodendrocytes, microglia/macrophages, and endothelial cells are included. Genes with FPKM values over 1 in mouse adult astrocytes are considered shared by both human and mouse astrocytes and genes with FPKM values under 1 in mouse adult astrocytes are considered unique to human astrocytes. Top 40 genes with highest expression in human astrocytes are listed.

| Top 40 Shared Human and Mouse Astrocyte Genes | Top 40 Human Specific Astrocyte Genes |
| --- | --- |
| DIO2 | OLFM2 |
| FGFR3 | IL17D |

TABLE 2

Supplemental Table 1. Patient information

| Specimen ID | Age (year, except in*) | Diagnosis | Brain region |
| --- | --- | --- | --- |
| 1 | 8 | Epilepsy | Anterior temporal lobe cortex |
| 2 | 13 | Epilepsy | Anterior temporal lobe cortex |
| 3 | 16 | Epilepsy | Anterior temporal lobe cortex |
| 4 | 21 | Epilepsy | Anterior temporal lobe cortex |
| 5 | 22 | Epilepsy | Anterior temporal lobe cortex |
| 6 | 35 | Epilepsy | Anterior temporal lobe cortex |
| 7 | 47 | Epilepsy | Anterior temporal lobe cortex |
| 8 | 51 | Epilepsy | Anterior temporal lobe cortex |
| 9 | 53 | Epilepsy | Anterior temporal lobe cortex |
| 10 | 60 | Epilepsy | Anterior temporal lobe cortex |
| 11 | 63 | Epilepsy | Anterior temporal lobe cortex |
| 12 | 63 | Epilepsy | Anterior temporal lobe cortex |
| 13 | 21 | Epilepsy | Hippocampus |
| 14 | 22 | Epilepsy | Hippocampus |
| 15 | 51 | Epilepsy | Hippocampus |
| 16 | 53 | Epilepsy | Hippocampus |
| 17 | 59 | Glioblastoma | Cortex, tumor core |
| 18 | 59 | Glioblastoma | Cortex, tumor peripheral region |
| 19 | 61 | Glioblastoma | Cortex, tumor core |
| 20 | 61 | Glioblastoma | Cortex, tumor peripheral region |
| 21 | 65 | Glioblastoma | Cortex, tumor core |
| 22 | 21 month* | Tumor | Cerebellum, tumor peripheral region |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for isolation of functional, quiescent human astrocytes, the method comprising:

contacting a complex population of human brain cells comprising astrocytes with at least one negative selection antibody or lectin that selectively binds a non-astrocyte lineage selected from anti-CD45; anti-GalC, anti-O4, anti-CD90 and *Banderiaea simplicifolia* lectin 1 (BSL-1) and collecting the eluate containing non-selected cells; and contacting the selected cell population with an antibody that specifically binds to HepaCAM, and collecting cells bound to the antibody;

to generate a purified population of astrocytes.

2. The method of claim 1, wherein the complex population of cells is not subject to in vitro expansion in the presence of serum.

3. The method of claim 1, wherein the negative selection reagent depletes from the complex cell population one or more of macrophages, microglia, neurons, oligodendrocytes, oligodendrocyte precursor cells, and endothelial cells.

4. The method of claim 1, wherein negative selection is performed with a cocktail comprising each of anti-CD45; anti-GalC, anti-O4, anti-CD90 and *Banderiaea simplicifolia* lectin 1 (BSL-1).

5. The method of claim 1, wherein the selection is performed by immunopanning.

6. The method of claim 1, wherein the resulting astrocyte population is at least 90% pure.

7. The method of claim 1, wherein the complex cell population is a brain tissue sample.

8. The method of claim 7, wherein the brain tissue is selected from the group consisting of: cerebral cortex, cerebellum, hippocampus, mesencephalon, striatum, and retina.

9. The method of claim 7, wherein the brain tissue is dissociated in the presence of a high concentration of papain for at least 30 minutes.

10. The method of claim 1, wherein the complex cell population is an in vitro cell culture.

* * * * *